United States Patent
Nicholas et al.

(10) Patent No.: US 10,080,552 B2
(45) Date of Patent: Sep. 25, 2018

(54) ADAPTER ASSEMBLY WITH GIMBAL FOR INTERCONNECTING ELECTROMECHANICAL SURGICAL DEVICES AND SURGICAL LOADING UNITS, AND SURGICAL SYSTEMS THEREOF

(71) Applicant: COVIDIEN LP, Mansfield, MA (US)

(72) Inventors: David Nicholas, Trumbull, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 1193 days.

(21) Appl. No.: 14/257,063

(22) Filed: Apr. 21, 2014

(65) Prior Publication Data

US 2015/0297199 A1  Oct. 22, 2015

(51) Int. Cl.
*A61B 17/00* (2006.01)
*A61B 17/29* (2006.01)

(52) U.S. Cl.
CPC .............. *A61B 17/00* (2013.01); *A61B 17/29* (2013.01); *A61B 2017/003* (2013.01); *A61B 2017/0046* (2013.01); *A61B 2017/00323* (2013.01); *A61B 2017/00367* (2013.01); *A61B 2017/2927* (2013.01)

(58) Field of Classification Search
CPC . A61B 17/00; A61B 17/29; A61B 2017/2927; A61B 2017/0046; A61B 2017/00323; A61B 2017/003; A61B 2017/00367
See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |

(Continued)

FOREIGN PATENT DOCUMENTS

| | | |
|---|---|---|
| AU | 2008229795 A1 | 4/2009 |
| CA | 2451558 A1 | 1/2003 |

(Continued)

OTHER PUBLICATIONS

European Search Report corresponding to EP 15164205 dated Aug. 24, 2015.

(Continued)

*Primary Examiner* — Hemant M Desai
*Assistant Examiner* — Mobeen Ahmed

(57) ABSTRACT

The present disclosure relates to adapter assemblies for use with and to electrically and mechanically interconnect electromechanical surgical devices and surgical loading units, and to surgical systems including hand held electromechanical surgical devices and adapter assemblies for connecting surgical loading units to the hand held electromechanical surgical devices.

20 Claims, 18 Drawing Sheets

(56) References Cited

U.S. PATENT DOCUMENTS

| | | |
|---|---|---|
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A * | 7/1997 | Green ............... A61B 17/07207 227/175.2 |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,013,991 A | 1/2000 | Philipp |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 * | 12/2004 | Hillstead .......... A61B 17/07207 227/175.1 |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 * | 9/2006 | Wales ............... A61B 17/07207 227/175.1 |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |

(56) References Cited

U.S. PATENT DOCUMENTS

| | | |
|---|---|---|
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0043718 A1* | 2/2005 | Madhani ............ A61B 19/2203 606/1 |
| 2005/0131442 A1 | 6/2005 | Yachia et al. |
| 2006/0095074 A1* | 5/2006 | Lee ................. A61B 17/29 606/205 |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0106317 A1* | 5/2007 | Shelton, IV ...... A61B 17/07207 606/170 |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0221701 A1* | 9/2007 | Ortiz ................ A61B 17/068 227/175.1 |
| 2007/0299387 A1* | 12/2007 | Williams ........... A61B 1/00052 604/22 |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0046000 A1* | 2/2008 | Lee ................. A61B 17/29 606/205 |
| 2008/0058801 A1 | 3/2008 | Taylor et al. |
| 2008/0064921 A1* | 3/2008 | Larkin .............. A61B 1/00087 600/104 |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |

(56) References Cited

U.S. PATENT DOCUMENTS

| | | | |
|---|---|---|---|
| 2008/0308603 A1* | 12/2008 | Shelton | A61B 17/07207 227/175.1 |
| 2009/0090763 A1 | 4/2009 | Zemlok et al. | |
| 2009/0099876 A1 | 4/2009 | Whitman | |
| 2009/0138006 A1 | 5/2009 | Bales et al. | |
| 2009/0171147 A1 | 7/2009 | Lee et al. | |
| 2009/0182193 A1 | 7/2009 | Whitman et al. | |
| 2009/0209990 A1 | 8/2009 | Yates et al. | |
| 2009/0254094 A1 | 10/2009 | Knapp et al. | |
| 2010/0022837 A1* | 1/2010 | Ishiguro | A61B 17/29 600/127 |
| 2010/0069942 A1 | 3/2010 | Shelton, IV | |
| 2010/0193568 A1 | 8/2010 | Scheib et al. | |
| 2010/0211053 A1 | 8/2010 | Ross et al. | |
| 2010/0225073 A1 | 9/2010 | Porter et al. | |
| 2011/0006101 A1 | 1/2011 | Hall et al. | |
| 2011/0017801 A1 | 1/2011 | Zemlok et al. | |
| 2011/0071508 A1 | 3/2011 | Duval et al. | |
| 2011/0077673 A1 | 3/2011 | Grubac et al. | |
| 2011/0121049 A1 | 5/2011 | Malinouskas et al. | |
| 2011/0125138 A1 | 5/2011 | Malinouskas et al. | |
| 2011/0139851 A1 | 6/2011 | McCuen | |
| 2011/0155783 A1 | 6/2011 | Rajappa et al. | |
| 2011/0155786 A1 | 6/2011 | Shelton, IV | |
| 2011/0172648 A1 | 7/2011 | Jeong | |
| 2011/0174099 A1 | 7/2011 | Ross et al. | |
| 2011/0184459 A1* | 7/2011 | Malkowski | A61B 17/29 606/206 |
| 2011/0204119 A1 | 8/2011 | McCuen | |
| 2011/0218522 A1 | 9/2011 | Whitman | |
| 2011/0253765 A1 | 10/2011 | Nicholas et al. | |
| 2011/0276057 A1 | 11/2011 | Conlon et al. | |
| 2011/0277776 A1* | 11/2011 | McGrogan | A61B 17/3423 128/852 |
| 2011/0290854 A1 | 12/2011 | Timm et al. | |
| 2011/0295242 A1* | 12/2011 | Spivey | A61B 17/07207 606/1 |
| 2011/0295269 A1 | 12/2011 | Swensgard et al. | |
| 2012/0000962 A1 | 1/2012 | Racenet et al. | |
| 2012/0074199 A1 | 3/2012 | Olson et al. | |
| 2012/0089131 A1 | 4/2012 | Zemlok et al. | |
| 2012/0104071 A1 | 5/2012 | Bryant | |
| 2012/0116368 A1 | 5/2012 | Viola | |
| 2012/0143002 A1 | 6/2012 | Aranyi et al. | |
| 2012/0172924 A1 | 7/2012 | Allen, IV | |
| 2012/0223121 A1 | 9/2012 | Viola et al. | |
| 2012/0245428 A1 | 9/2012 | Smith et al. | |
| 2012/0253326 A1* | 10/2012 | Kleyman | A61B 34/71 606/1 |
| 2012/0253329 A1 | 10/2012 | Zemlok et al. | |
| 2012/0310220 A1 | 12/2012 | Malkowski et al. | |
| 2012/0323226 A1 | 12/2012 | Chowaniec et al. | |
| 2012/0330285 A1 | 12/2012 | Hartoumbekis et al. | |
| 2013/0018361 A1 | 1/2013 | Bryant | |
| 2013/0093149 A1 | 4/2013 | Saur et al. | |
| 2013/0098966 A1 | 4/2013 | Kostrzewski et al. | |
| 2013/0098968 A1 | 4/2013 | Aranyi et al. | |
| 2013/0098969 A1 | 4/2013 | Scirica et al. | |
| 2013/0181035 A1 | 7/2013 | Milliman | |
| 2013/0184704 A1 | 7/2013 | Beardsley et al. | |
| 2013/0214025 A1 | 8/2013 | Zemlok et al. | |
| 2013/0240596 A1 | 9/2013 | Whitman | |
| 2013/0274722 A1 | 10/2013 | Kostrzewski et al. | |
| 2013/0282052 A1 | 10/2013 | Aranyi et al. | |
| 2013/0292451 A1 | 11/2013 | Viola et al. | |
| 2013/0313304 A1 | 11/2013 | Shelton, IV et al. | |
| 2013/0317486 A1 | 11/2013 | Nicholas et al. | |
| 2013/0317522 A1* | 11/2013 | Nishizawa | A61B 17/2909 606/130 |
| 2013/0319706 A1 | 12/2013 | Nicholas et al. | |
| 2013/0324978 A1 | 12/2013 | Nicholas et al. | |
| 2013/0324979 A1 | 12/2013 | Nicholas et al. | |
| 2013/0334281 A1 | 12/2013 | Williams | |
| 2014/0012236 A1 | 1/2014 | Williams et al. | |
| 2014/0012237 A1 | 1/2014 | Pribanic et al. | |
| 2014/0012238 A1 | 1/2014 | Chen et al. | |
| 2014/0012289 A1 | 1/2014 | Snow et al. | |
| 2014/0025046 A1 | 1/2014 | Williams et al. | |
| 2014/0110455 A1 | 4/2014 | Ingmanson et al. | |
| 2014/0114403 A1 | 4/2014 | Dale et al. | |
| 2014/0144970 A1 | 5/2014 | Aranyi et al. | |
| 2014/0207125 A1 | 7/2014 | Applegate et al. | |
| 2014/0207182 A1 | 7/2014 | Zergiebel et al. | |
| 2014/0207185 A1 | 7/2014 | Goble et al. | |
| 2014/0236173 A1 | 8/2014 | Scirica et al. | |
| 2014/0236174 A1 | 8/2014 | Williams et al. | |
| 2014/0276932 A1 | 9/2014 | Williams et al. | |
| 2014/0299647 A1 | 10/2014 | Scirica et al. | |
| 2014/0303668 A1 | 10/2014 | Nicholas et al. | |
| 2014/0358129 A1 | 12/2014 | Zergiebel et al. | |
| 2014/0361068 A1 | 12/2014 | Aranyi et al. | |
| 2014/0373652 A1 | 12/2014 | Zergiebel et al. | |
| 2015/0048144 A1 | 2/2015 | Whitman | |
| 2015/0076205 A1 | 3/2015 | Zergiebel | |
| 2015/0080912 A1 | 3/2015 | Sapre | |
| 2015/0157321 A1 | 6/2015 | Zergiebel et al. | |
| 2015/0164502 A1 | 6/2015 | Richard et al. | |
| 2015/0272577 A1 | 10/2015 | Zemlok et al. | |
| 2015/0297199 A1 | 10/2015 | Nicholas et al. | |
| 2015/0303996 A1 | 10/2015 | Calderoni | |
| 2015/0320420 A1 | 11/2015 | Penna et al. | |
| 2015/0327850 A1 | 11/2015 | Kostrzewski | |
| 2015/0342601 A1 | 12/2015 | Williams et al. | |
| 2015/0342603 A1 | 12/2015 | Zergiebel et al. | |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0067000 A1* | 3/2016 | Johnston | A61B 34/71 606/130 |
| 2016/0095585 A1 | 4/2016 | Zergiebel et al. | |
| 2016/0095596 A1 | 4/2016 | Scirica et al. | |
| 2016/0106406 A1* | 4/2016 | Cabrera | A61B 17/1155 606/1 |
| 2016/0113648 A1 | 4/2016 | Zergiebel et al. | |
| 2016/0113649 A1 | 4/2016 | Zergiebel et al. | |
| 2016/0184040 A1* | 6/2016 | Sholev | A61B 34/71 606/130 |
| 2016/0296216 A1* | 10/2016 | Nicholas | A61B 17/00 |

FOREIGN PATENT DOCUMENTS

| | | | |
|---|---|---|---|
| CA | 2824590 A1 | 4/2014 | |
| CN | 101856251 A | 10/2010 | |
| CN | 102247182 A | 11/2011 | |
| DE | 102008053842 A1 | 5/2010 | |
| EP | 0634144 A1 | 1/1995 | |
| EP | 0648476 A1 | 4/1995 | |
| EP | 0686374 A2 | 12/1995 | |
| EP | 0705571 A1 | 4/1996 | |
| EP | 1690502 A1 | 8/2006 | |
| EP | 1723913 A1 | 11/2006 | |
| EP | 1736112 A1 | 12/2006 | |
| EP | 1759652 A2 | 3/2007 | |
| EP | 1769754 A1 | 4/2007 | |
| EP | 1772105 A1 | 4/2007 | |
| EP | 1 813 203 A2 | 8/2007 | |
| EP | 1813199 A1 | 8/2007 | |
| EP | 1813211 A2 | 8/2007 | |
| EP | 1908412 A2 | 4/2008 | |
| EP | 1917929 A1 | 5/2008 | |
| EP | 1943954 A2 | 7/2008 | |
| EP | 1943956 A2 | 7/2008 | |
| EP | 1943958 A1 | 7/2008 | |
| EP | 1943976 A2 | 7/2008 | |
| EP | 1952769 A2 | 8/2008 | |
| EP | 2005898 A2 | 12/2008 | |
| EP | 2027819 A1 | 2/2009 | |
| EP | 2044890 A1 | 4/2009 | |
| EP | 2055243 A2 | 5/2009 | |
| EP | 2090247 A1 | 8/2009 | |

(56) References Cited

FOREIGN PATENT DOCUMENTS

| | | |
|---|---|---|
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| ES | 2333509 A1 | 2/2010 |
| FR | 2861574 A1 | 5/2005 |
| JP | 08-038488 | 2/1996 |
| JP | 2005-125075 A | 5/2005 |
| KR | 20120022521 A | 3/2012 |
| WO | 99/15086 A1 | 4/1999 |
| WO | 2000/072760 A1 | 12/2000 |
| WO | 2000/072765 A1 | 12/2000 |
| WO | 2003/000138 A2 | 1/2003 |
| WO | 2003/026511 A1 | 4/2003 |
| WO | 2003/030743 A2 | 4/2003 |
| WO | 2003065916 A1 | 8/2003 |
| WO | 2003/077769 A1 | 9/2003 |
| WO | 2003090630 A2 | 11/2003 |
| WO | 2004/107989 A1 | 12/2004 |
| WO | 2006/042210 A2 | 4/2006 |
| WO | 2007016290 A2 | 2/2007 |
| WO | 2007/026354 A1 | 3/2007 |
| WO | 2007137304 A2 | 11/2007 |
| WO | 2008/008178 A2 | 1/2008 |
| WO | 2008/020964 A2 | 2/2008 |
| WO | 2008/131362 A2 | 10/2008 |
| WO | 2008/133956 A2 | 11/2008 |
| WO | 2009039506 A1 | 3/2009 |
| WO | 2007014355 A3 | 4/2009 |
| WO | 2009/132359 A2 | 10/2009 |
| WO | 2009/143092 A1 | 11/2009 |
| WO | 2009149234 A1 | 12/2009 |
| WO | 2010/112609 A1 | 10/2010 |
| WO | 2011/108840 A2 | 9/2011 |
| WO | 2012040984 A1 | 4/2012 |

OTHER PUBLICATIONS

European Search Report dated Feb. 25, 2016, corresponding to European Application No. 15190752.4; 8 pages.
Extended European Search Report issued in corresponding EP 17162090.9 dated Jul. 4, 2017.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.

* cited by examiner

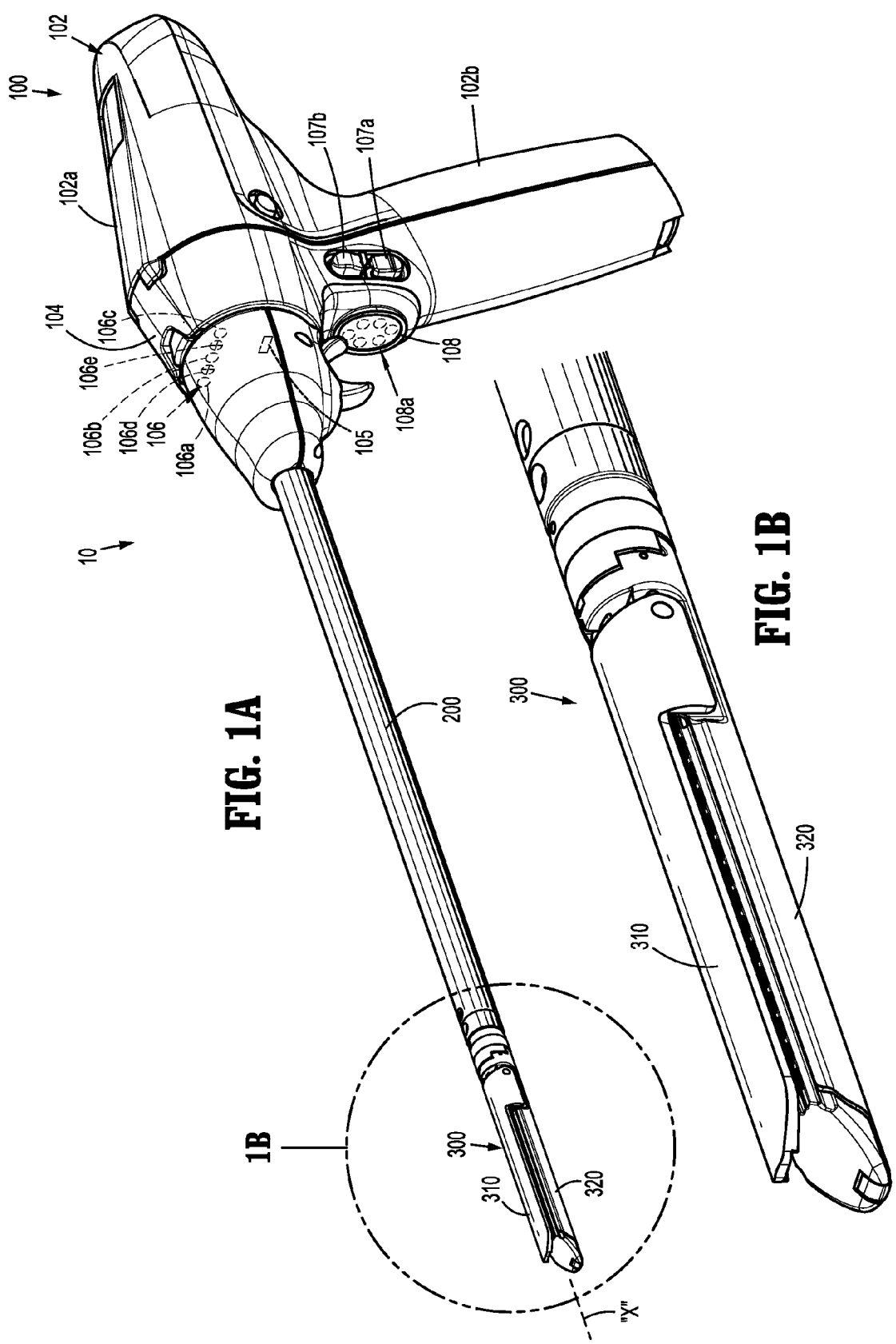

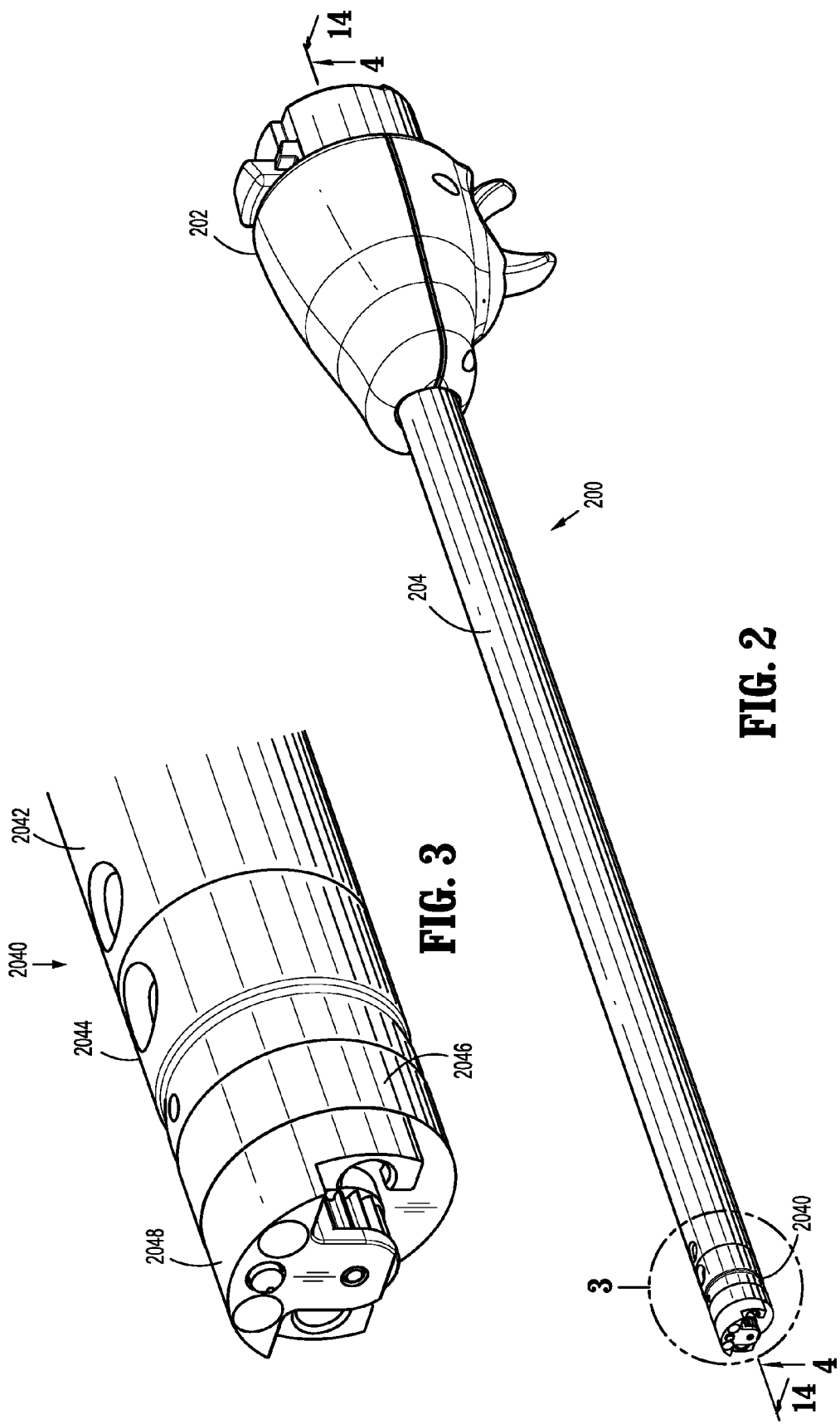

ADAPTER ASSEMBLY WITH GIMBAL FOR INTERCONNECTING ELECTROMECHANICAL SURGICAL DEVICES AND SURGICAL LOADING UNITS, AND SURGICAL SYSTEMS THEREOF

TECHNICAL FIELD

The present disclosure relates to adapter assemblies for use in surgical systems. More specifically, the present disclosure relates to adapter assemblies for use with and to electrically and mechanically interconnect electromechanical surgical devices and surgical loading units, and to surgical systems including hand held electromechanical surgical devices and adapter assemblies for connecting surgical loading units to the hand held electromechanical surgical devices.

BACKGROUND

A number of surgical device manufacturers have developed product lines with proprietary powered drive systems for operating and/or manipulating the surgical device. In many instances the surgical devices include a powered handle assembly, which is reusable, and a disposable end effector or the like that is selectively connected to the powered handle assembly prior to use and then disconnected from the end effector following use in order to be disposed of or in some instances sterilized for re-use.

Many of the existing end effectors for use with many of the existing powered surgical devices and/or handle assemblies are driven by a linear force. For examples, end effectors for performing endo-gastrointestinal anastomosis procedures, end-to-end anastomosis procedures and transverse anastomosis procedures, each typically require a linear driving force in order to be operated. As such, these end effectors are not compatible with surgical devices and/or handle assemblies that use a rotary motion to deliver power or the like.

In order to make the linear driven end effectors compatible with powered surgical devices and/or handle assemblies that use a rotary motion to deliver power, adapters and/or adapter assemblies are used to interface between and interconnect the linear driven end effectors with the powered rotary driven surgical devices and/or handle assemblies. Many of these adapter and/or adapter assemblies are complex devices including many parts and requiring extensive labor to assemble. Accordingly, a need exists to develop adapters and/or adapter assemblies that incorporate fewer parts, are less labor intensive to assemble, and are ultimately more economical to manufacture.

SUMMARY

The present disclosure relates to adapter assemblies for use with and to electrically and mechanically interconnect electromechanical surgical devices and surgical loading units, and to surgical systems including hand held electromechanical surgical devices and adapter assemblies for connecting surgical loading units to the hand held electromechanical surgical devices.

According to an aspect of the present disclosure, an adapter assembly for selectively interconnecting a surgical loading unit that is configured to perform a function and a surgical device that is configured to actuate the surgical loading unit, the surgical loading unit including an axially translatable drive member, and the surgical device including a plurality of rotatable drive shafts, is provided.

The adapter assembly includes a housing configured and adapted for connection with the surgical device and to be in operative communication with each rotatable drive shaft of the plurality of rotatable drive shafts of the surgical device. An outer tube has a proximal end supported by the housing and a distal end configured and adapted for connection with the surgical loading unit. The distal end of the outer tube is in operative communication with the axially translatable drive member of the surgical loading unit. The outer tube defines a longitudinal axis. The outer tube can include a distal housing assembly configured and adapted to engage a proximal end of the surgical loading unit.

An articulation assembly includes a gimbal supported in the outer tube and a plurality of threaded sleeves supported in the housing. The plurality of threaded sleeves is coupled to the gimbal by at least one cable. In embodiments, the plurality of threaded sleeves is supported on at least one threaded screw. Rotation of at least one of the plurality of rotatable drive shafts of the surgical device translates at least two of the plurality of threaded sleeves to omni-directionally articulate the gimbal relative to the longitudinal axis of the outer tube with the at least one cable. Articulation of the gimbal articulates the surgical loading unit about the distal end of the outer tube. The gimbal can include a distal flange configured and adapted to engage the distal housing assembly to enable the surgical loading unit to articulate in response to movement of the gimbal. In embodiments, the gimbal defines at least one slot in an outer surface thereof. The at least one cable is secured within the at least one slot.

The adapter assembly includes a firing shaft having a proximal end configured and adapted to couple to at least one of the plurality of rotatable drive shafts of the surgical device and a distal end configured and adapted to couple to the axially translatable drive member of the surgical loading unit to enable firing of the surgical loading unit.

In embodiments, the firing shaft is configured and adapted to transmit a rotational force through the gimbal to effectuate axially translation of the axially translatable drive member and fire the surgical loading unit. In some embodiments, the firing shaft includes a proximal firing shaft and a distal firing shaft. The proximal and distal firing shafts can be coupled together within the gimbal such that the distal firing shaft is movable relative to the proximal firing shaft. The proximal firing shaft can include a ball member on a distal end thereof and the distal firing shaft can include a socket on a proximal end thereof. The socket defines a socket bore and the ball member of the proximal firing shaft can be mounted within the socket bore.

In some embodiments, the gimbal defines a gimbal bore therethrough configured and adapted to receive the distal firing shaft such that the gimbal and the distal firing shaft are movable about an outer surface of the ball member.

In embodiments, the at least one threaded screw includes a first set of threads and a second set of threads. The first and second set of threads can be threaded in opposite directions. A first one of the plurality of threaded sleeves can be threadably engaged with the first set of threads and a second one of the plurality of threaded sleeves can be threadably engaged with the second set of threads. Rotation of the at least one threaded screw in a first rotational direction can approximate the first one and the second one of the plurality of threaded sleeves. Rotation of the at least one threaded screw in a second rotational direction can separate the first one and the second one of the plurality of threaded sleeves.

In embodiments, a firing trigger is secured to the adapter assembly. The firing trigger can be secured to the housing.

According to another aspect of the present disclosure, an electromechanical surgical system is provided. The electromechanical surgical system includes a surgical loading unit including at least one axially translatable drive member and a handle-held electromechanical surgical device. The handle-held electromechanical surgical device includes a housing and at least one rotatable drive shaft supported in the housing.

An adapter assembly is selectively connectable between the housing of the surgical device and the surgical loading unit. The adapter assembly includes an articulation assembly and a firing shaft.

The articulation assembly includes a gimbal and a plurality of threaded sleeves. The plurality of threaded sleeves is coupled to the gimbal by at least one cable. The plurality of threaded sleeves is movable to articulate the gimbal with the at least one cable. Articulation of the gimbal articulates the surgical loading unit.

The firing shaft is connectable between the at least one rotatable drive shaft of the surgical device and the at least one axially translatable drive member. The firing shaft is movable with the gimbal to omni-directionally articulate the surgical loading unit and rotatable to translate the at least one axially translatable drive member through the surgical loading unit.

According to another aspect of the present disclosure, a method of articulating a surgical loading unit operatively coupled to a surgical device by an adapter is provided. The method includes rotating at least one rotatable drive shaft of the surgical device to rotate at least one threaded screw supported within the adapter and axially translate a plurality of threaded sleeves along the at least one threaded screw, translating a plurality of cables secured between the plurality of threaded sleeves and a gimbal, and articulating the gimbal with the plurality of cables to articulate the surgical loading unit relative to adapter. The method can involve rotating a firing shaft to fire the surgical loading unit.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 1A is a perspective view of an electromechanical surgical system in accordance with the principles of the present disclosure;

FIG. 1B is an enlarged, perspective view of the indicated area of detail shown in FIG. 1A;

FIG. 2 is an enlarged, perspective view of an adapter assembly of the electromechanical surgical system of FIG. 1A;

FIG. 3 is an enlarged, perspective view of a distal portion of the adapter assembly of FIG. 2;

DETAILED DESCRIPTION

Figure 4:
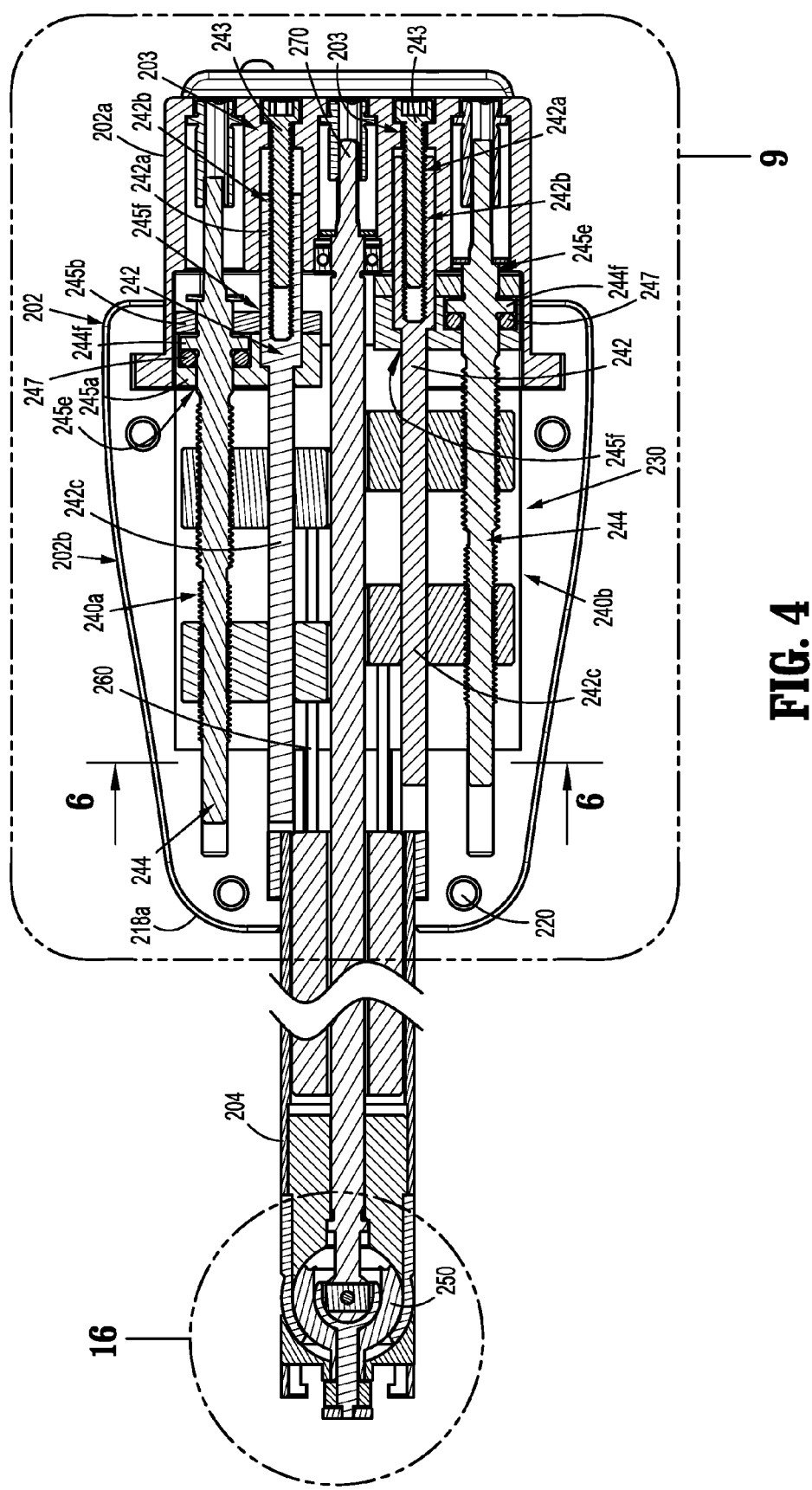
FIG. 4 is a bottom, cross-sectional view the adapter assembly of FIG. 2, as taken along line 4-4 of FIG. 2, illustrating an articulation assembly thereof in a first condition.

Electromechanical surgical systems of the present disclosure include surgical devices in the form of powered hand held electromechanical instruments configured for selective attachment to a plurality of different end effectors that are each configured for actuation and manipulation by the powered hand held electromechanical surgical instrument. In particular, the presently described electromechanical surgical systems include adapter assemblies that interconnect the powered hand held electromechanical surgical instruments to the plurality of different end effectors. Each adapter assembly includes an articulation assembly that is operatively coupled to a powered hand held electromechanical surgical instrument for effectuating actuation and/or manipulation thereof. The articulation assembly includes one or more cables that interconnect a gimbal and two or more threaded sleeves. The gimbal couples to one of the plurality of end effectors such that axial movement of the threaded sleeves moves the one or more cables to rotate the gimbal and effectuate articulation of the end effector about a distal end of the adapter assembly.

Embodiments of the presently disclosed electromechanical surgical systems, surgical devices/handle assemblies, adapter assemblies, and/or loading units are described in detail with reference to the drawings, in which like reference numerals designate identical or corresponding elements in each of the several views. As used herein the term "distal" refers to that portion of the system, assembly, device, and/or component thereof, farther from the user, while the term "proximal" refers to that portion of the system, assembly, device, and/or component thereof, closer to the user.

Turning now to FIGS. 1A and 1B, an electromechanical surgical system, in accordance with the present disclosure, generally referred to as 10, includes a surgical device 100 in the form of a powered hand held electromechanical instrument, an adapter assembly 200, and a loading unit 300 (e.g., an end effector, multiple- or single-use loading unit). Surgical device 100 is configured for selective connection with adapter assembly 200, and, in turn, adapter assembly 200 is configured for selective connection with loading unit 300. Together, surgical device 100 and adapter assembly 200 may cooperate to actuate loading unit 300.

Surgical device 100 includes a handle housing 102 including a circuit board (not shown) and a drive mechanism (not shown) situated therein. The circuit board is configured to control the various operations of surgical device 100. Handle housing 102 defines a cavity therein (not shown) for selective removable receipt of a rechargeable battery (not shown) therein. The battery is configured to supply power to any of the electrical components of surgical device 100.

Handle housing 102 includes an upper housing portion 102a which houses various components of surgical device 100, and a lower hand grip portion 102b extending from upper housing portion 102a. Lower hand grip portion 102b may be disposed distally of a proximal-most end of upper housing portion 102a. The location of lower housing portion 102b relative to upper housing portion 102a is selected to balance a weight of a surgical device 100 that is connected to or supporting adapter assembly 200 and/or loading unit 300.

Handle housing 102 provides a housing in which the drive mechanism is situated. The drive mechanism is configured to drive shafts and/or gear components in order to perform the various operations of surgical device 100. In particular, the drive mechanism is configured to drive shafts and/or gear components in order to selectively articulate loading unit 300 about a longitudinal axis "X" and relative to a distal end of adapter assembly 200, to selectively rotate loading unit 300 about longitudinal axis "X" and relative to handle housing 102, to selectively move/approximate/separate an anvil assembly 310 and a cartridge assembly 320 of loading unit 300 relative to one another, and/or to fire a stapling and cutting cartridge within cartridge assembly 320 of loading unit 300.

Handle housing 102 defines a connection portion 104 configured to accept a proximal end of adapter assembly 200. Connection portion 104 houses a trigger contact surface 105 in electrical communication with the circuit board and a plurality of rotatable drive shafts or connectors 106. Each rotatable drive shaft of the plurality of rotatable drive shafts can be independently, and/or dependently, actuatable and rotatable by the drive mechanism (not shown) housed within housing handle 102. In embodiments, the plurality of rotatable drive shafts 106 includes rotatable drive shafts, 106a, 106b, 106c, 106d, and 106e arranged in a common plane or line with one another. As can be appreciated, the plurality of rotatable drive shafts can be arranged in any suitable configuration. The drive mechanism may be configured to selectively drive one of the rotatable drive shafts 106 of surgical instrument 100, at a given time.

Handle housing 102 supports a plurality of finger-actuated control buttons, rocker devices and the like for activating various functions of surgical device 100. For example, handle housing 102 supports a plurality of actuators including, for example, an articulating pad such as articulating pad 108, to effectuate articulation of end effector 300 as will be described in greater detail below. Articulating pad 108 is configured to contact a plurality of sensors 108a that cooperate with articulating pad 108 to enable omni-directional articulation of loading unit 300 relative to adapter assembly 200. In embodiments, one or more of the plurality of sensors 108a correspond to different yaw and/or pitch angles, relative to longitudinal axis "X," to which loading unit 300 can be moved, upon activation of one or more of the plurality of sensors 108a in response to depression of different portions of articulating pad 108. Handle housing 102 can support actuators 107a, 107b, which as will be described in great detail below, can be disposed in electrical communication with rotatable drive shafts 106d, 106e for actuation thereof to enable adjustment of one or more of the components of adapter assembly 200. Any of the presently described actuators can have any suitable configuration (e.g., button, knob, toggle, slide etc.)

Reference may be made to International Application No. PCT/US2008/077249, filed Sep. 22, 2008 (Inter. Pub. No. WO 2009/039506), and U.S. Patent Application Publication No. 2011/0121049, filed on Nov. 20, 2009, the entire contents of each of which being incorporated herein by reference, for a detailed description of various internal components of and operation of exemplary electromechanical surgical systems, the components of which are combinable and/or interchangeable with one or more components of electromechanical surgical systems 10 described herein.

With reference to FIGS. 2 and 3, adapter assembly 200 includes a housing 202 at a proximal end portion thereof and an outer tube 204 that extends distally from housing 202 to a distal end portion 2040 thereof.

Turning now to FIGS. 4-9, housing 202 of adapter assembly 200 includes a proximal housing 202a and a distal housing 202b that support a firing trigger 205. Firing trigger 205 includes a trigger contact surface 205a and is slidably disposed in proximal housing 202a. Proximal housing 202a includes a housing body 206 defining a central slot 206a therethrough and having a distal lip 206b extending radially outwardly therefrom. Housing body 206 supports a mounting assembly 210 thereon and includes an elongate tongue 208 extending distally therefrom that defines an elongate channel 208a that slidably receives firing trigger 205.

Mounting assembly 210 is supported on housing body 206 and includes a shaft 212 that extends outwardly from housing body 206, a spring 214 that is supported about an outer surface of shaft 212, and a mounting button 216 that engages spring 214 and shaft 212. Spring 214 contacts a bottom surface of mounting button 216 to bias mounting button 216 upwardly to an extended position spaced from housing body 206. Spring 214 is sufficiently compressible to enable mounting button 216 to be depressed downwardly from the extended position to a compressed position. In the compressed position, mounting button 216 is disposed in close approximation with housing body 206 and offset from the extended position. Mounting button 216 includes sloped engagement features 216a that are configured to contact connection portion 104a (FIG. 1A) of handle housing 102 while mounting button 216 is in the extended position to facilitate securement of housing 202 to connection portion 104 of handle housing 102.

Figure 5:
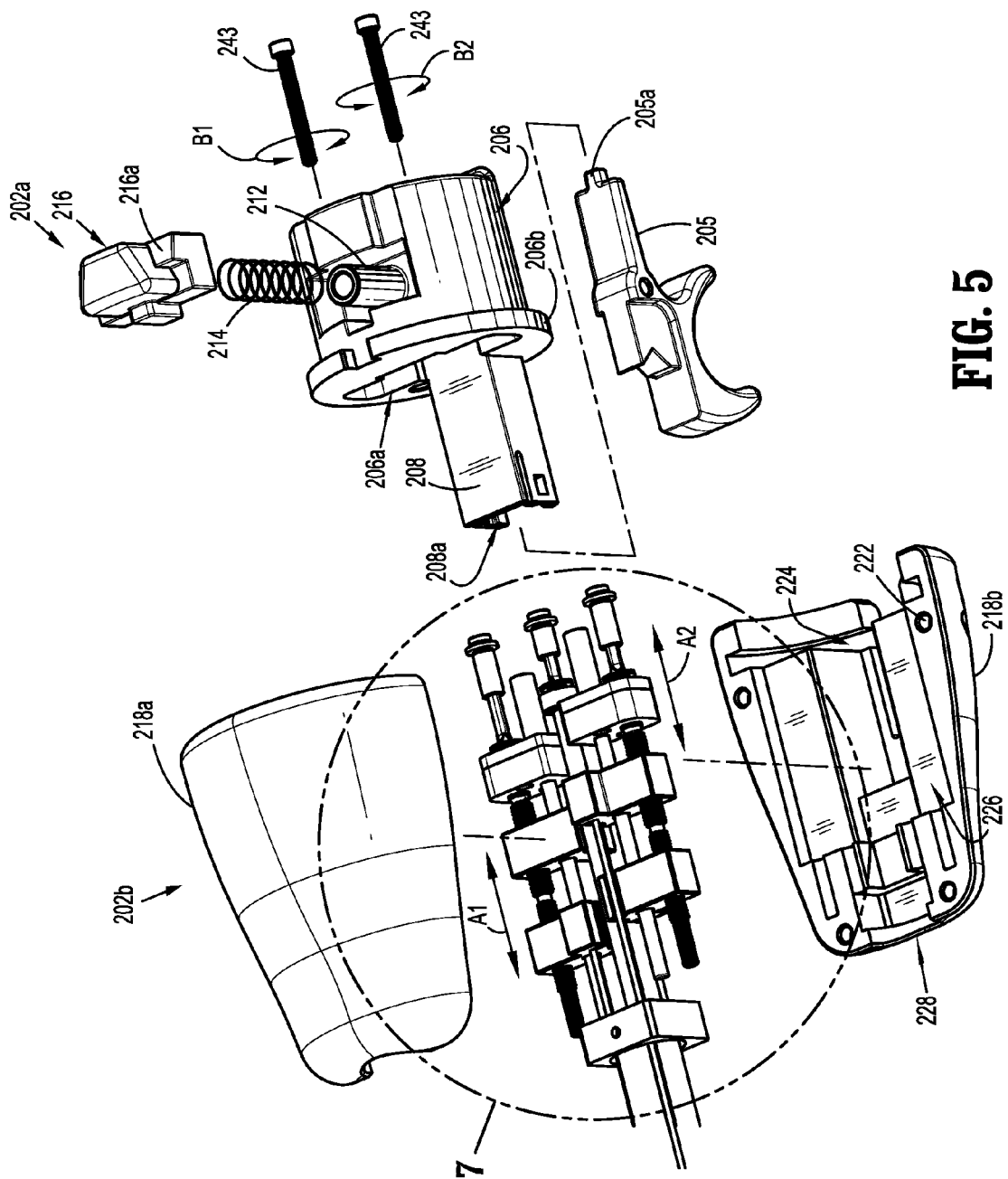
FIG. 5 is a side, perspective view, with parts separated, of a proximal portion of the adapter assembly of FIG. 2.

As seen in FIGS. 4 and 5, distal housing 206b includes a first half-section 218a and a second half-section 218b. First half-section 218a includes a plurality of pins 220 extending therefrom and second half-section 218b defines a plurality of bores 222 adapted to receive the plurality of pins 220 of first half-section 218a to mate the first and second half-sections 218a, 218b together. Each of first and second half-sections 218a, 218b defines an internal lip receiving annular recess 224 adapted to receive a portion of distal lip 206b of proximal housing 202a to facilitate securement of proximal and distal housings 202a, 202b. Each of first and second half-sections 218a, 218b defines an articulation-assembly-receiving recess 226 that is in communication with an outer-tube-receiving channel 228. Each outer-tube-receiving channel 228 is defined through a distal end of one of first and second half-sections 218a, 218b.

Figure 6:
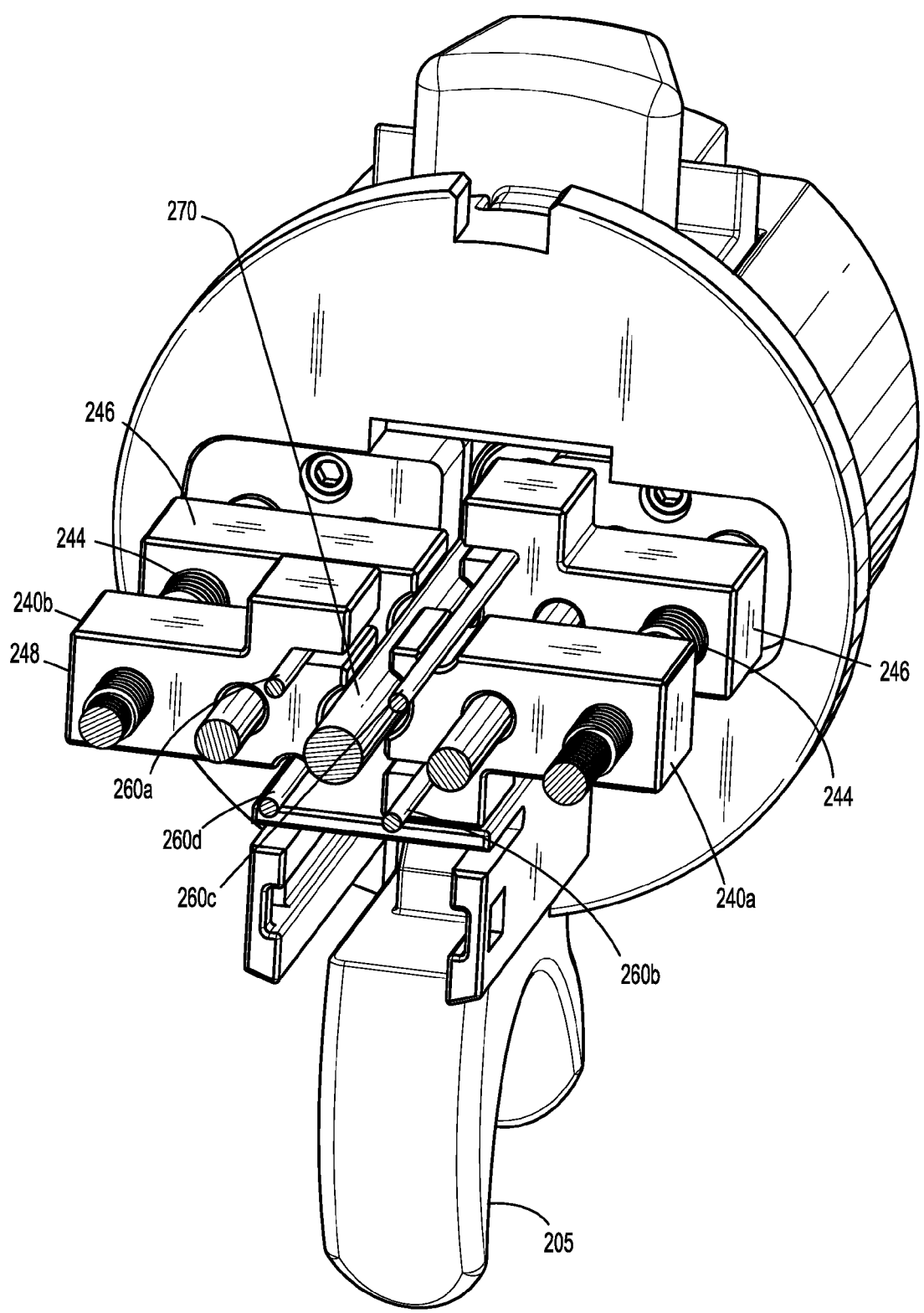
FIG. 6 is front, perspective view of the proximal portion of the adapter assembly of FIG. 2, as taken along line 6-6 of FIG. 4.

An articulation assembly 230 is supported within housing 202 and outer tube 204. Articulation assembly 230 includes a pair of sleeve assemblies 240a, 240b at a proximal end thereof and a gimbal 250 at a distal end thereof. The pair of sleeve assemblies 240a, 240b and gimbal 250 is connected by a plurality of cables 260. As depicted in FIG. 6, and described in greater detail below, the plurality of cables 260 includes a first cable 260a, a second cable 260b, a third cable 260c, and a fourth cable 260d.

Figure 7:
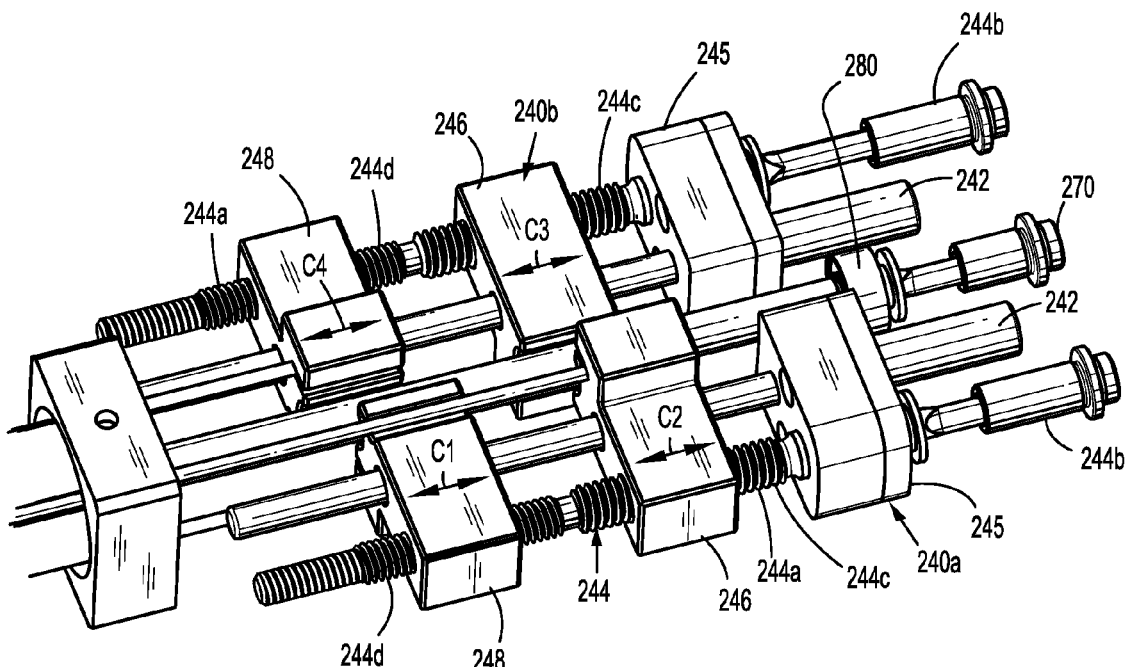
FIG. 7 is an enlarged, side perspective view of a portion of the articulation assembly and a portion of a firing assembly, with the articulation assembly shown in the first condition.
Figure 8:
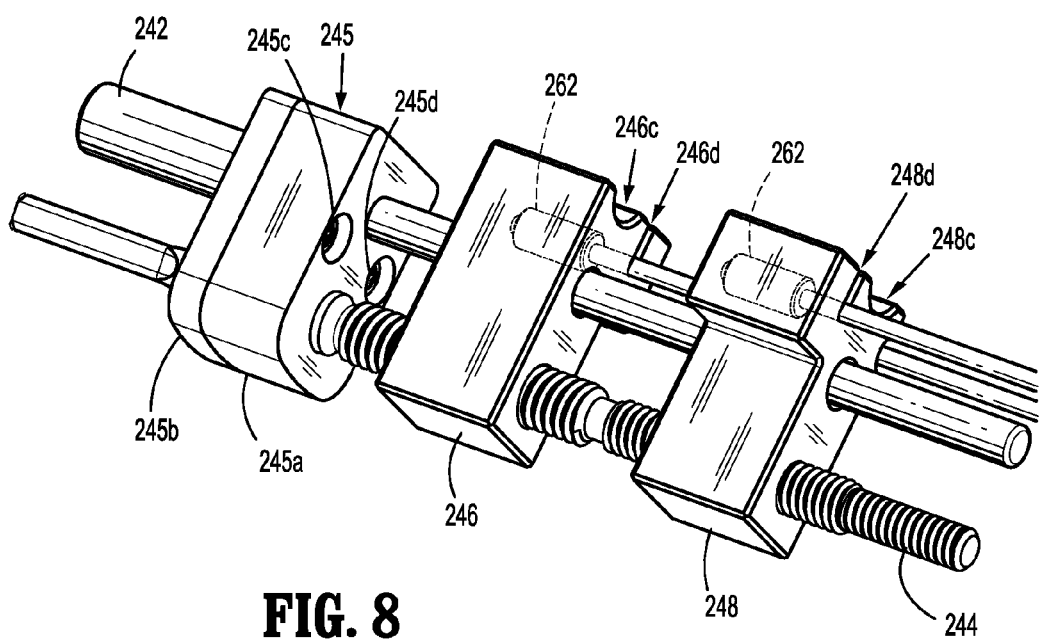
FIG. 8 is an enlarged, bottom perspective view of a section of the portion of the articulation assembly shown in FIG. 7.

With reference to FIGS. 6-8, each of the pair of sleeve assemblies 240a, 240b includes a support shaft 242, a threaded screw assembly 244, a bearing block 245, and a pair of threaded sleeves 246, 248.

As seen in FIG. 4, support shaft 242 includes a proximal portion 242a received in central slot 206a (see FIG. 5) of proximal housing 202a. Proximal portion 242a defines a threaded bore 242b therein. Each threaded bore 242b receives therein a screw 243 that is advanced through a screw passage 203 defined in proximal housing 202a to facilitate securement of articulation assembly 230 to proximal housing 202a. Support shaft 242 further includes a distal portion 242c that extends distally from proximal portion 242a.

With reference to FIG. 5, each screw 243 can function as a cable tensioner to adjust overall slack in one or more of the plurality of cables 260 as depicted by axial lines of translation "A1" and "A2" of the pair of sleeve assemblies 240a, 240b and by rotational arrows "B1" and "B2" of screws 243. For example, with reference again to FIG. 4, the pair of sleeve assemblies 240a, 240b are disposed in offset longitudinal relationship with respect to each other (e.g., compare relative longitudinal relationship between bearing blocks 245 and/or distal ends of threaded screw assemblies 244) to depict differences in slack adjustment in each sleeve assembly 240a, 240b. In embodiments, slack adjustments of one of the pair of sleeve assemblies 240a, 240b can be different and/or the same as the other of the pair of sleeve assemblies 240a, 240b, and likewise can be further adjusted as necessary to achieve a desired cable slack in one or more of the plurality of cables 260. In particular, tightening and/or loosening rotation of screw 243 relative to one of threaded bores 242b approximates and/or separates screw 243 relative to support shaft 242 to axially move one or both of the pair of sleeve assemblies 240a, 240b (proximally and/or distally) to adjust tension in one or more of the plurality of cables 260. In embodiments, tightening of one or both screws 243 draws one or both of the pair of sleeve assemblies 240a, 240b proximally, and loosening of one or both screws distally advances one or both of the pair of sleeve assemblies 240a, 240b. In some embodiments, loosening of one or both screws 243 draws one or both of the pair of sleeve assemblies 240a, 240b proximally, and tightening of one or both of the pair of sleeve assemblies 240a, 240b. As can be appreciated, each screw 243 can be independently and/or dependently rotatable (e.g., tightening rotation, loosening rotation, clockwise rotation, and/or counterclockwise rotation) with respect to the other screw 243.

Threaded screw assembly 244 includes a threaded screw 244a extending distally from an input socket 244b with a distal end of input socket 244b being mechanically coupled to a proximal end of threaded screw 244a. Each input socket 244b is configured to engage one of the plurality of rotatable drive shafts 106 of handle housing 102. For example, input socket 244b of sleeve assembly 240b can be mechanically coupled to rotatable drive shaft 106a and input socket 244b of sleeve assembly 240a can be mechanically coupled to rotatable drive shaft 106c.

Threaded screw 244a includes a first thread 244c and a second thread 244d that are threaded in opposite directions. For example, first thread 244c can be a left-hand thread and second thread 244d can be a right-hand thread, and vice versa. In embodiments, first and second threads 244c, 244d have the same thread pitch. Threaded screw 244a can include a third thread 244e. Third thread 244e can be either right or left handed and can have the same and/or different pitch as the first and/or second threads 244c, 244d. As can be appreciated, any of first, second, or third threads 244c, 244d, 244e can have any suitable shape, dimension, and/or configuration. With reference to FIG. 4, threaded screw 244 includes a retaining member 244f extending from an outer surface thereof. Retaining member 244f can have a plurality of opposed sections. In some embodiments, retaining member 244f is an annular lip.

As seen in FIG. 8, bearing block 245 is mounted on proximal end portion of support shaft 242 and on threaded screw assembly 244. Bearing block 245 includes distal plate 245a and a proximal plate 245b that are secured together by a pair of fasteners 245c, 245d. With reference also to FIG. 4, distal and proximal plates 245a, 245b define first and second channels 245e, 245f therethrough. First channel 245e receives a proximal portion of threaded screw 244 and encloses retaining member 244f and a thrust bearing 247. Second channel 245f receives support shaft 242, which can be fixedly secured therein to facilitate axial advancement of one of the pair of sleeve assemblies 240a, 240b upon rotation of screws 243 as described above. As can be appreciated, bearing block 245 of sleeve assembly 240a is a mirror image of bearing block 245 of sleeve assembly 240b.

Figure 9:
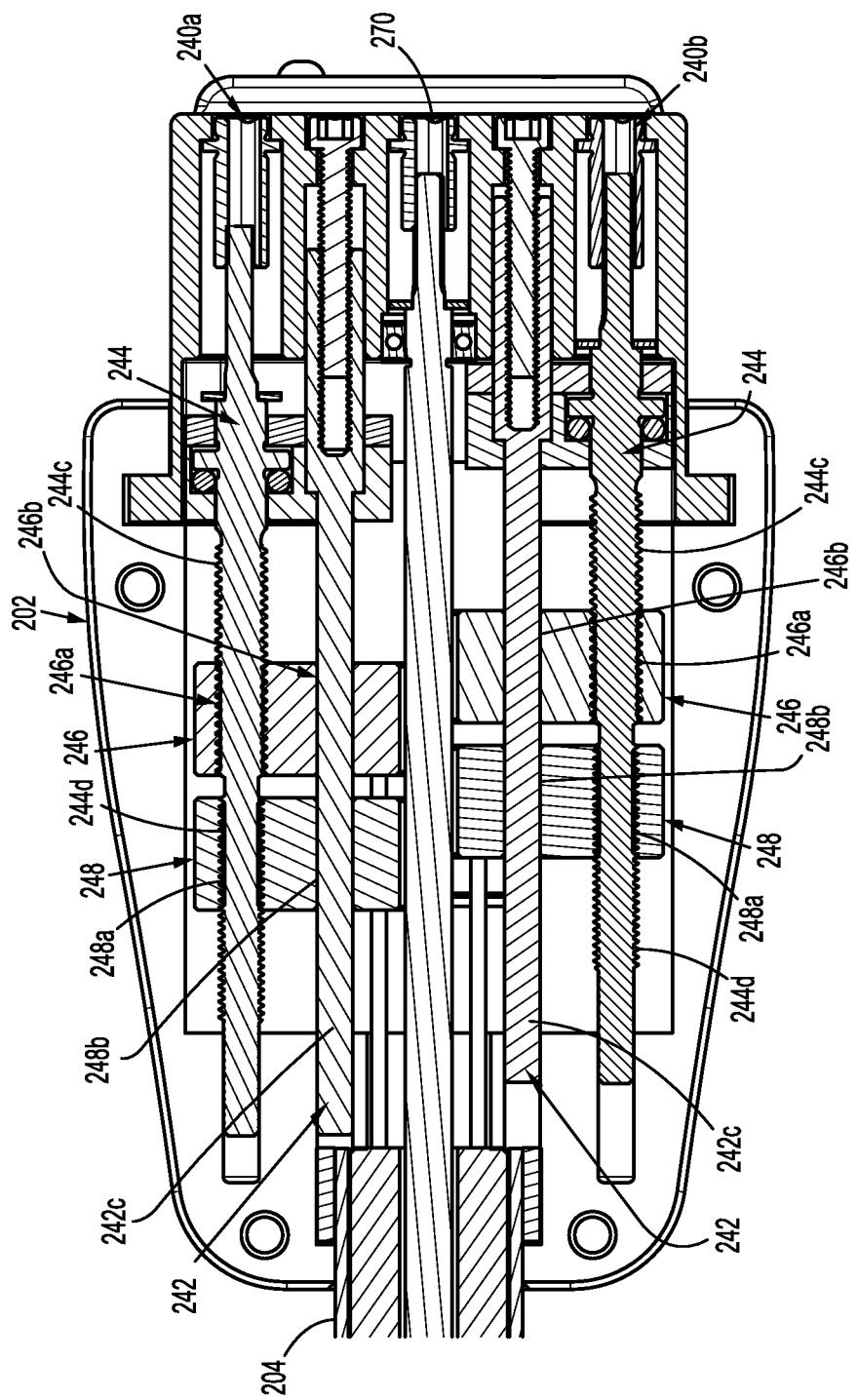
FIG. 9 is an enlarged, cross-sectional, bottom view of the indicated area of detail shown in FIG. 4, with the articulation assembly being shown in a second condition.

Referring to FIGS. 7 and 8, each of the pair of threaded sleeves 246, 248 has an L-shaped profile. As illustrated in FIG. 9, threaded sleeve 246 defines first and second bores 246a, 246b therethrough with first bore 246a being threaded and second bore 246b being smooth. Similarly, threaded sleeve 248 defines first and second bores 248a, 248b therethrough with first bore 248a being threaded and second bore 248b being smooth. Each of the pair of sleeve assemblies 240a, 240b is arranged so that threaded bores 246a, 248a receive threaded screw 244a such that first thread 244c threadably engages threaded bore 246a and such that second thread 244d threadably engages threaded bore 248a. Each of the pair of sleeve assemblies 240a, 240b is also arranged so that smooth bores 246b, 248b of threaded sleeves 246, 248 receive distal portion 242c of support shaft 242 such that threaded sleeves 246, 248 move axially along distal portion 242c of support shaft 242. In embodiments, threaded sleeve 246 of sleeve assembly 240a can be disposed in mirrored relation with threaded sleeve 246 of sleeve assembly 240b. As seen in FIG. 8, each of the pair of threaded sleeves 246, 248 define shaft-receiving channels 246c, 248c and cable-receiving channels 246d, 248d in side surfaces thereof. Each of the pair of threaded sleeves 246, 248 is coupled to one of the plurality of cables 260 by a cable ferrule 262 connected to a proximal end of each of the plurality of cables 260. Cable-receiving channels 246d, 248d receive cable ferrule 262 of one of the plurality of cables 260 therein to secure one of the plurality of cables 260 to each of the pair of threaded sleeves 246, 248.

With reference to FIGS. 10-13, each of the plurality of cables 260 extends distally to a retaining ball 262 (see FIG. 13) to secure the distal end of the first, second, third, and fourth cables 260a-260d to gimbal 250. Each opposite pair of the plurality of cables 260 can have two cables that are secured to gimbal 250 at locations 180 degrees apart (e.g., first and fourth cables 260a, 260d or second and third cables 260b, 260c).

As seen in FIG. 6, each opposite pair of the plurality of cables 260 has proximal ends that connect to the pair of threaded sleeves 246, 248 on the same threaded screw 244. Thus, the proximal end of the first and fourth cables 260a, 260d connect to one threaded screw 244, and the proximal end of the second and third cables 260b, 260c connect to the other threaded screw 244. It is contemplated that one or more of the plurality of cables can criss-cross within outer tube 204.

Referring again to FIGS. 10-13, gimbal 250 has a proximal portion 250a with a generally rounded shape and a distal portion 250b extending from proximal portion 250a. Proximal portion 250a defines a plurality of ball-retaining slots 252 (e.g., four) in a distal outer surface thereof so that each ball-retaining slot of the plurality of ball-retaining slots 252 is dimensioned to receive one of retaining balls 262 of the plurality of cables 260 to secure each of the plurality of cables 260 to gimbal 250.

Proximal portion 250a of gimbal 250 includes a plurality of spaced apart wings 254 that extend from an outer surface thereof. Each wing of the plurality of spaced-apart wings 254 includes a top surface 254a and side surfaces 254b. Side surfaces 254b of adjacent wings of the plurality of spaced-apart wings 254 define a plurality of slots 256 about the outer surface of proximal portion 250a. The plurality of slots 256, which are configured to receive the plurality of cables 260, are in communication with the plurality of ball-retaining slots 252 and extend proximally therefrom.

Distal portion 250b of gimbal 250 includes a tubular shaft 251 having an upwardly depending flange 253 extending from an outer surface of tubular shaft 251. Upwardly depending flange 253 defines a pair of arcuate side channels 253a, 253b in side surfaces thereof. The pair of arcuate side channels 253a, 253b form a pair of opposed teeth 253c, 253d that extend from side surfaces of flange 253. Proximal and distal portions 250a, 250b of gimbal 250 define a gimbal bore 258 (see FIGS. 11-12) that extends therethrough and includes first section 258a defined by inner surfaces of distal portion 250b and a second section 258b defined by inner surfaces of proximal portion 250a.

Figure 14:
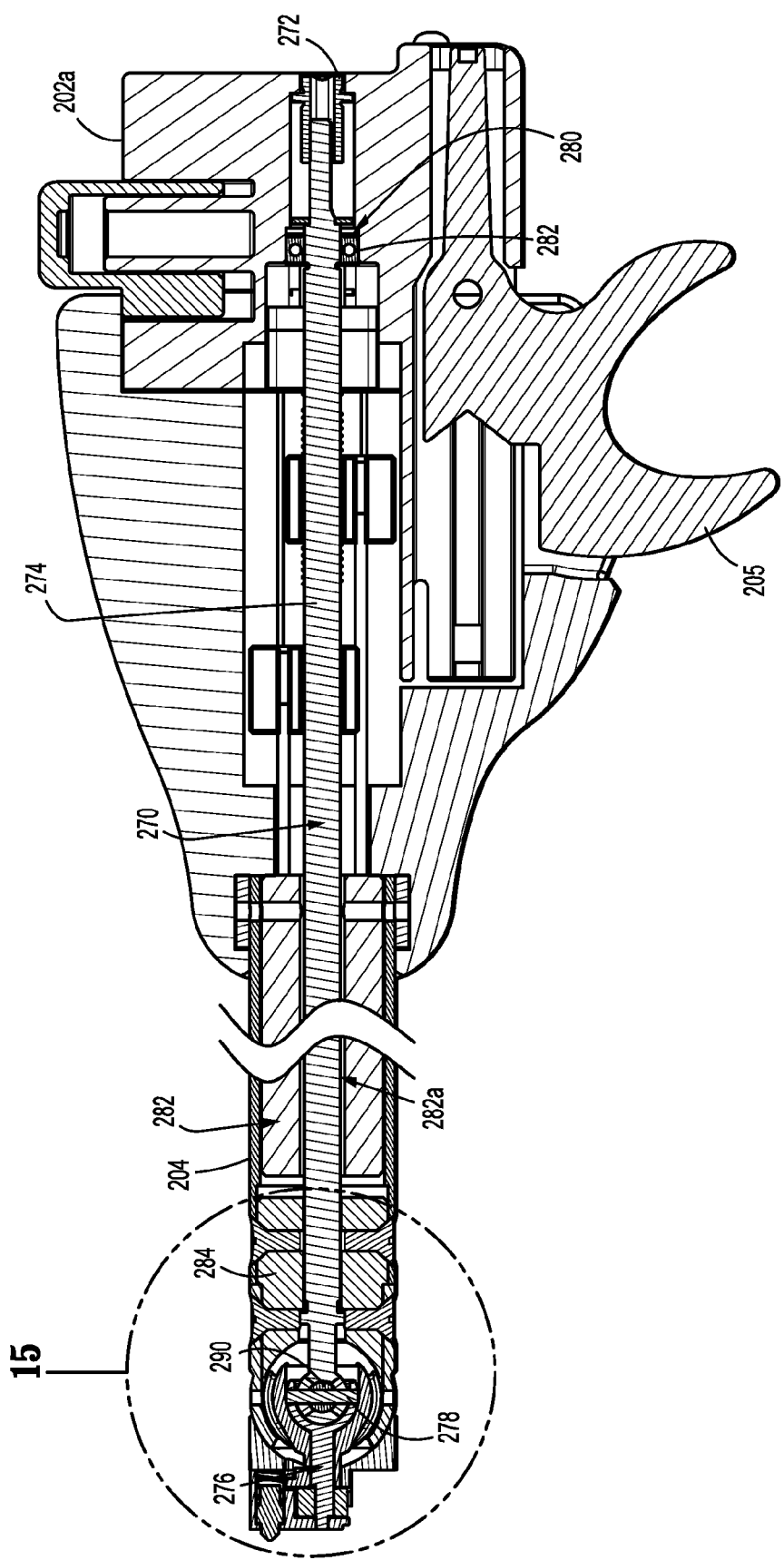
FIG. 14 is a side, cross-sectional view of the adapter assembly of FIG. 2, as taken along line 14-14 of FIG. 2.

Referring to FIG. 14, a firing assembly 270 is supported within housing 202 and outer tube 204 of adapter assembly 200. Firing assembly 270 includes an input socket 272 adapted to couple to rotatable drive shaft 106b of housing handle 102 (see FIG. 1A), a proximal firing shaft 274 extending distally from input socket 272, a distal firing shaft 276 extending distally from proximal firing shaft 274, and a pin 278 that secures proximal and distal firing shafts 274, 276 together within gimbal bore 258.

With continued reference to FIG. 14, a housing bearing member 280 supports a proximal end of proximal firing shaft 274 within proximal housing 202a, and proximal and distal mounting members 282, 284 support a distal end of proximal firing shaft 274 within outer tube 204. Housing bearing member 280 includes a thrust bearing 282 that receives proximal firing shaft 274 therethrough to enable proximal firing shaft 274 to rotate. Proximal mounting member 282 defines a central passage 282a therethrough that receives the proximal firing shaft 274.

Figure 10:
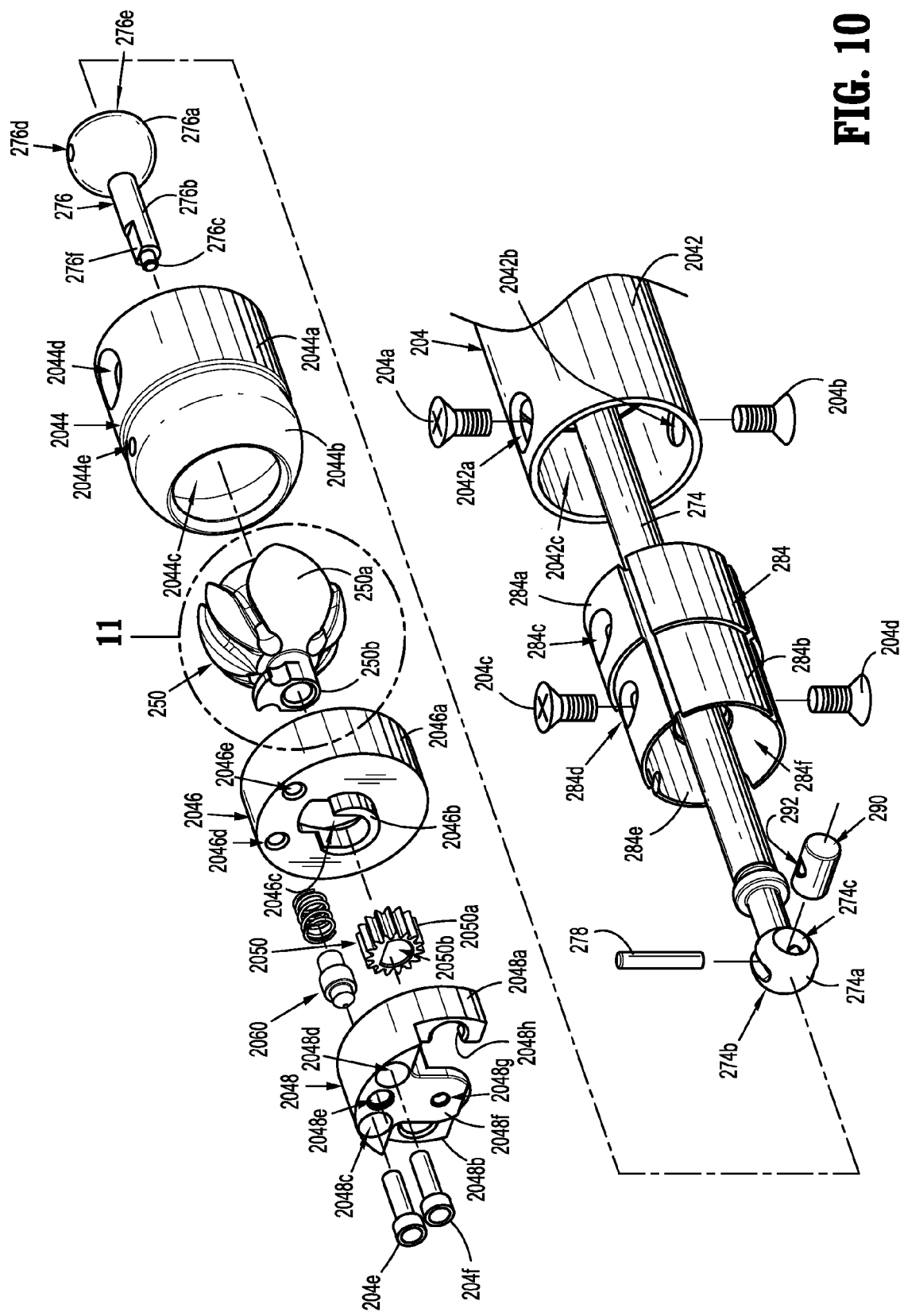
FIG. 10 is an enlarged, perspective view, with parts separated, of the distal portion of the adapter assembly shown in FIG. 3.
Figure 11:
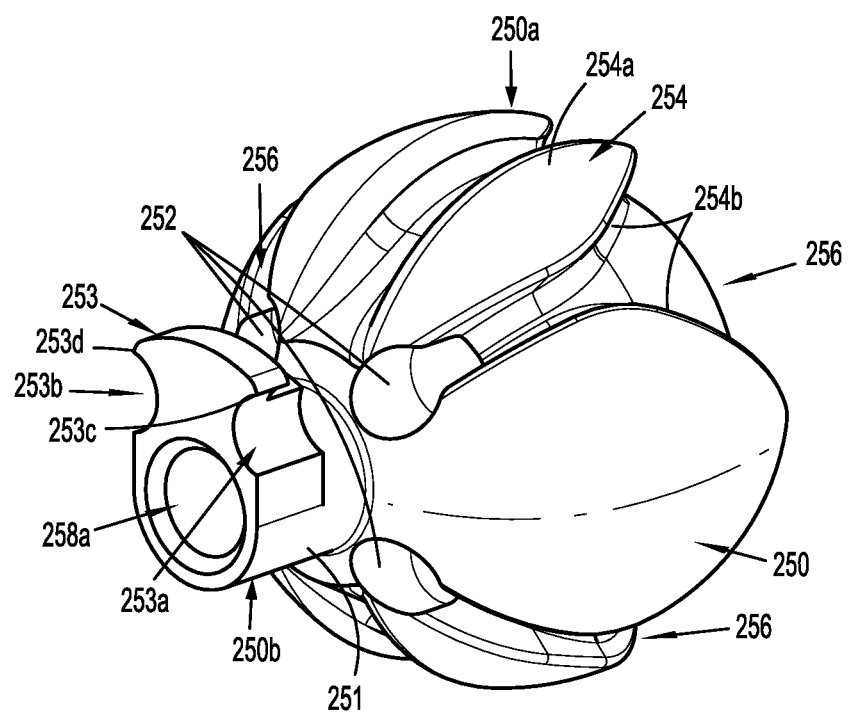
FIG. 11 is an enlarged, perspective view of a gimbal of the articulation assembly.
Figure 12:
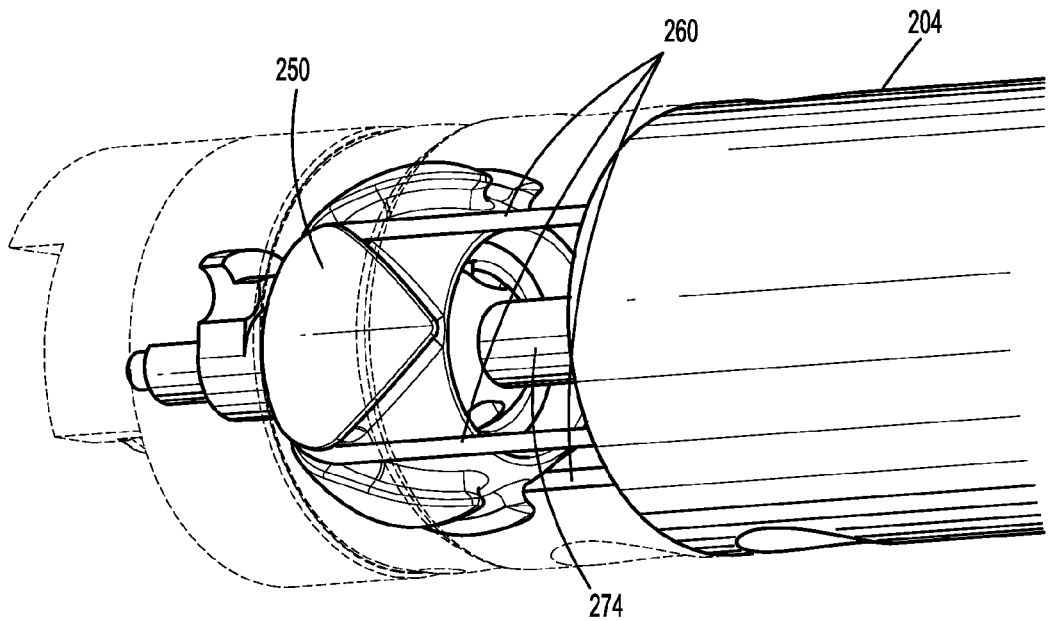
FIG. 12 is an enlarged, side, perspective view of the distal portion of the adapter assembly shown in FIG. 3, with portions thereof removed for clarity, the distal portion of the adapter assembly being shown in an non-articulated condition.
Figure 13:
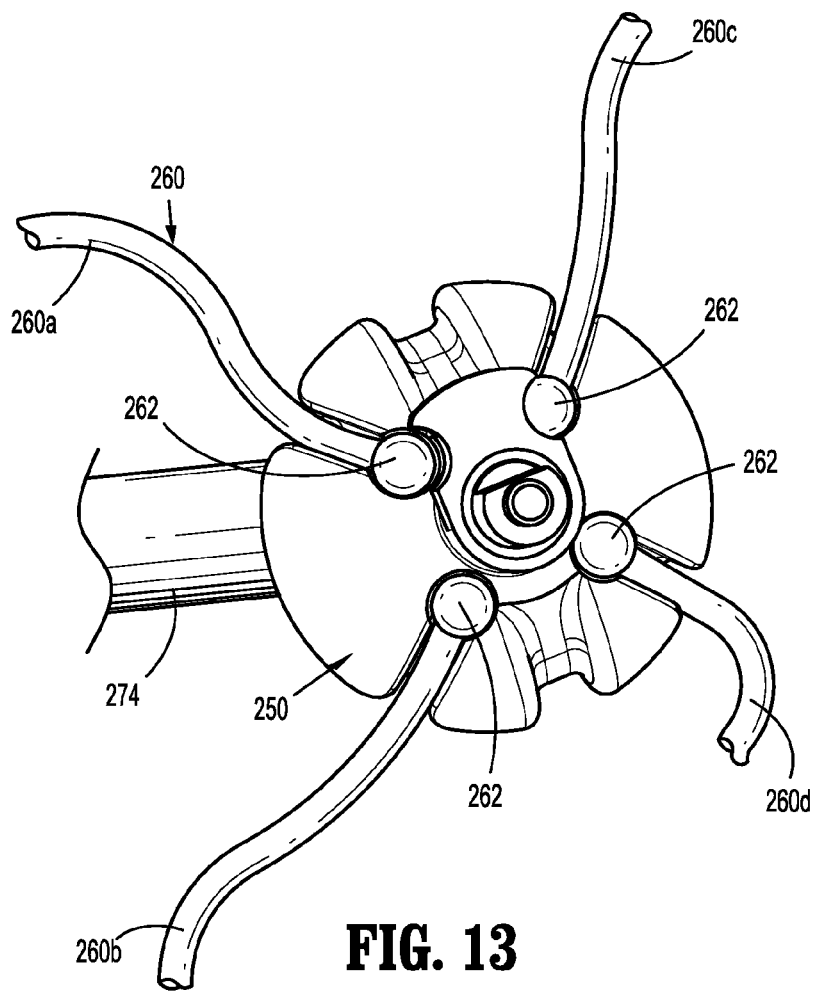
FIG. 13 is an enlarged, front, perspective view of a distal portion of the articulation assembly.
Figure 15:
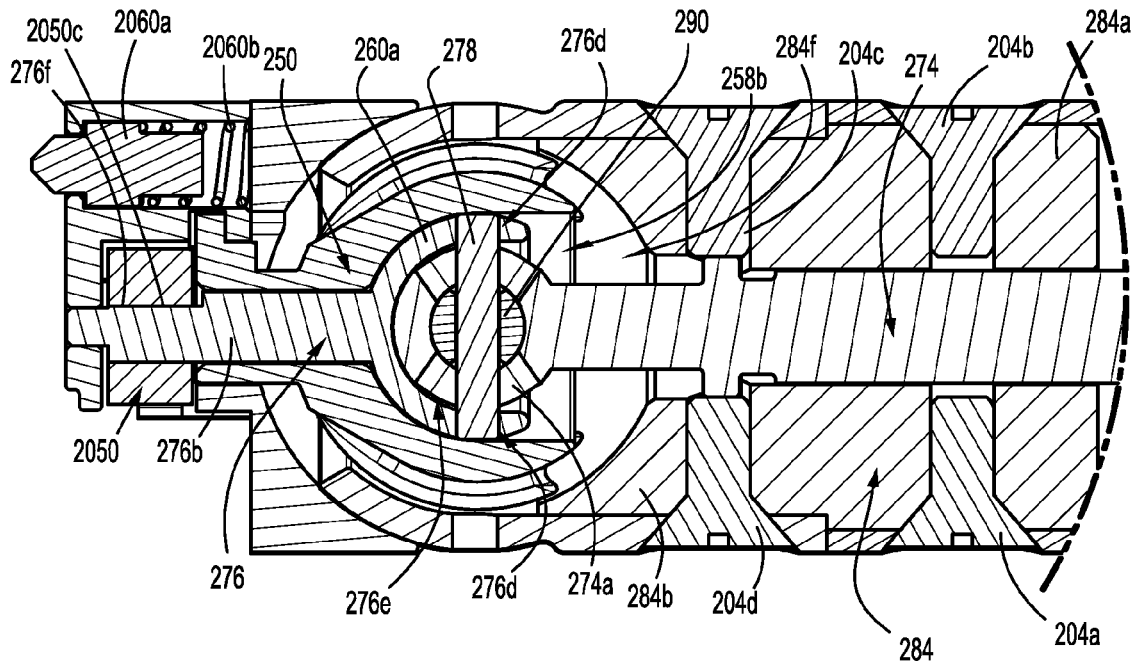
FIG. 15 is an enlarged, side, cross-sectional view of the indicated area of detail shown in FIG. 14.
Figure 16:
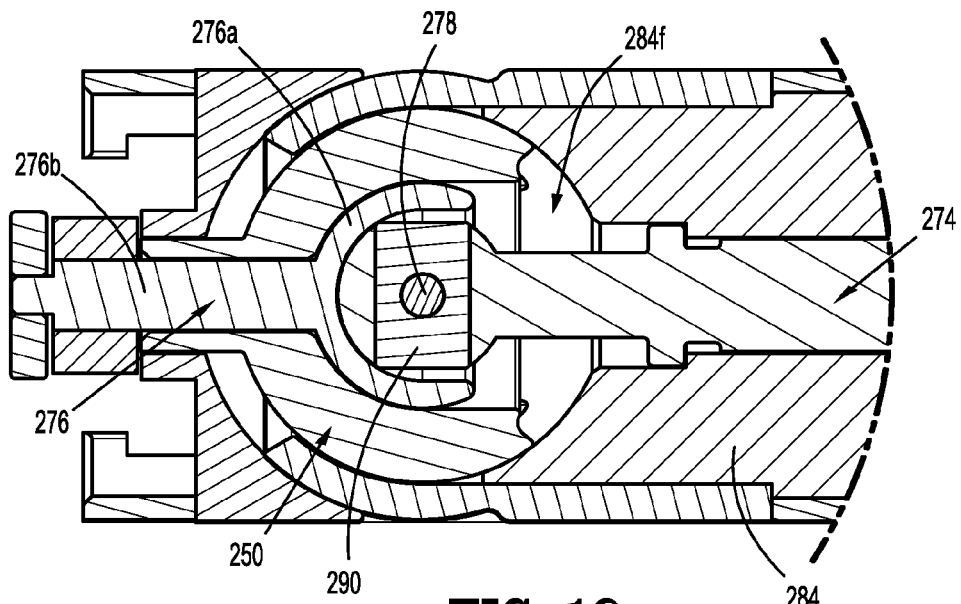
FIG. 16 is an enlarged, bottom, cross-sectional view of the indicated area of detail shown in FIG. 4.

As seen in FIGS. 10, 15, and 16, distal mounting member 284 includes a proximal section 284a and a distal section 284b. Proximal section 284a defines a pair of screw openings 284c therethrough with each of the pair of screw openings 284c being disposed on opposed top and bottom surfaces of proximal section 284a. Similarly, distal section 284b of distal mounting member 284 defines a pair of screw openings 284d therethrough with each of the pair of screw openings 284d being disposed on opposed top and bottom surfaces of distal section 284b. Distal section 284b of distal mounting member 284 further includes an inner surface 284e that defines a hemispherical opening 284f that receives proximal portion 250a of gimbal 250 to enable gimbal 250 to articulate omni-directionally therein.

Referring again to FIG. 14, the proximal end of proximal firing shaft 274 is received in a distal end of input socket 272, and the distal end of proximal firing shaft 274 includes a coupling member 274a. As seen in FIG. 10, coupling member 274a defines an elongate top slot 274b therethrough and a side slot 274c therethrough that is disposed transverse to top slot 274b. Elongate top slot 274b receives pin 278 and side slot 274c receives a pin coupling 290 defining a pin bore 292 therein that receives pin 278.

With continued reference to FIGS. 10 and 14-16, distal firing shaft 276 includes a proximal portion 276a having a hemispherical shape, a central shaft 276b extending distally from a distal end of proximal portion 276a, and a distal tip 276c extending distally from a distal end of central shaft 276b. Proximal portion 276a of distal firing shaft 276 defines a pin channel 276d that extends therethrough. Proximal portion 276a of distal firing shaft 276 has an inner surface that defines a hemispherical opening 276e adapted to receive coupling member 274a of proximal firing shaft 274. Central shaft 276b defines a ledge 276f that is recessed from a top surface of central shaft 276b.

As seen in FIGS. 3, 10, 15 and 16, distal end portion 2040 of outer tube 204 includes a first segment 2042, a second segment 2044, a third segment 2046, and a fourth segment 2048.

First segment 2042 of distal end portion 2040 of outer tube 204 defines a pair of screw openings 2042a, 2042b that correspond with the pair of screw openings 284c of distal mounting member 284. The pair of screw openings 2042a, 2042b of first segment 2042 and the pair of screw openings 284c of distal mounting member 284 receive a pair of screws 204a, 204b to secure proximal section 284a of distal mounting member 284 within an opening 2042c defined within a distal end of first segment 2042.

Second segment 2044 of distal end portion 2040 of outer tube 204 includes a proximal section 2044a, and a distal section 2044b that extends from proximal section 2044a. Second segment 2044 defines a central opening 2044c that extends through proximal and distal sections 2044a, 2044b. Proximal section 2044a defines a pair of screw openings 2044d therethrough with each of the pair of screw openings 2044d being disposed on opposed top and bottom surfaces of proximal section 2044a. The pair of screw openings 2044d of second segment 2044 corresponds with the pair of screw openings 284d of distal mounting member 284 so that a pair of screws 204c, 204d secures second segment 2044 over distal section 284b of distal mounting member 284. Distal section 2044b defines pin opening 2044e. Pin opening 2044e can be aligned with pin channel 276d of distal firing shaft 276 to enable pin 278 to be advanced therethrough for securement within pin coupling 290.

Third segment 2046 of distal end portion 2040 of outer tube 204 has a cylindrical body 2046a that mounts over distal section 2044b of second segment 2044 and covers pin opening 2044e thereof. Third segment 2046 includes a U-shaped shoe 2046b that extends distally from a distal surface of cylindrical body 2046a. A central channel 2046c is defined through U-shaped shoe 2046b and cylindrical body 2046a, and is configured to receive distal portion 250b of gimbal 250.

Fourth segment 2048 of distal end portion 2040 of outer tube 204 includes a pair of arms 2048a, 2048b that extends from fourth segment 2048. The pair of arms 2048a, 2048b are disposed in spaced apart and mirrored relation to one another. A pair of screw openings 2048c, 2048d is defined in fourth segment 2048 and are aligned with a pair of screw bores 2046d, 2046e defined within third segment 2046 so that a pair of screws 204e, 204f can be received by the pair of screw openings 2048c, 2048d of the fourth segment 2048 and the pair of screw bores 2046d, 2046e of the third segment 2046 to secure third and fourth segments 2046, 2048 together. Fourth segment 2048 defines a plunger opening 2048e that receives a plunger assembly 2060 of distal end portion 2040 of outer tube 204.

Plunger assembly 2060 includes a plunger 2060a that is biased through plunger opening 2048e by a spring 2060b (see FIG. 15). Plunger assembly 2060 and the pair of arms 2048a, 2048b cooperate to facilitate securement of the proximal end of loading unit 300 to distal end portion 2040 as described in greater detail below (see FIGS. 18A and 18B).

As illustrated in FIG. 10, a tongue 2048f depends from fourth segment 2048 and defines an opening 2048f therethrough that receives distal tip 276c of distal firing shaft 276 therethrough. Tongue 2048f supports a gear 2050 between a proximal surface of tongue 2048f and a distal surface of U-shaped shoe 2046b of third segment 2046 so that teeth 2050a extending from gear 2050 are positioned between mating surfaces 2048h of each of the pair of arms 2048a, 2048b of fourth segment 2048 of distal end portion 2040 of outer tube 204.

Inner surfaces of gear 2050 define a channel 2050b therethrough. Inner surfaces of gear 2050 include a flat surface 2050c (see FIG. 15) that is supported on ledge 276f of distal firing shaft 276.

Figure 17:
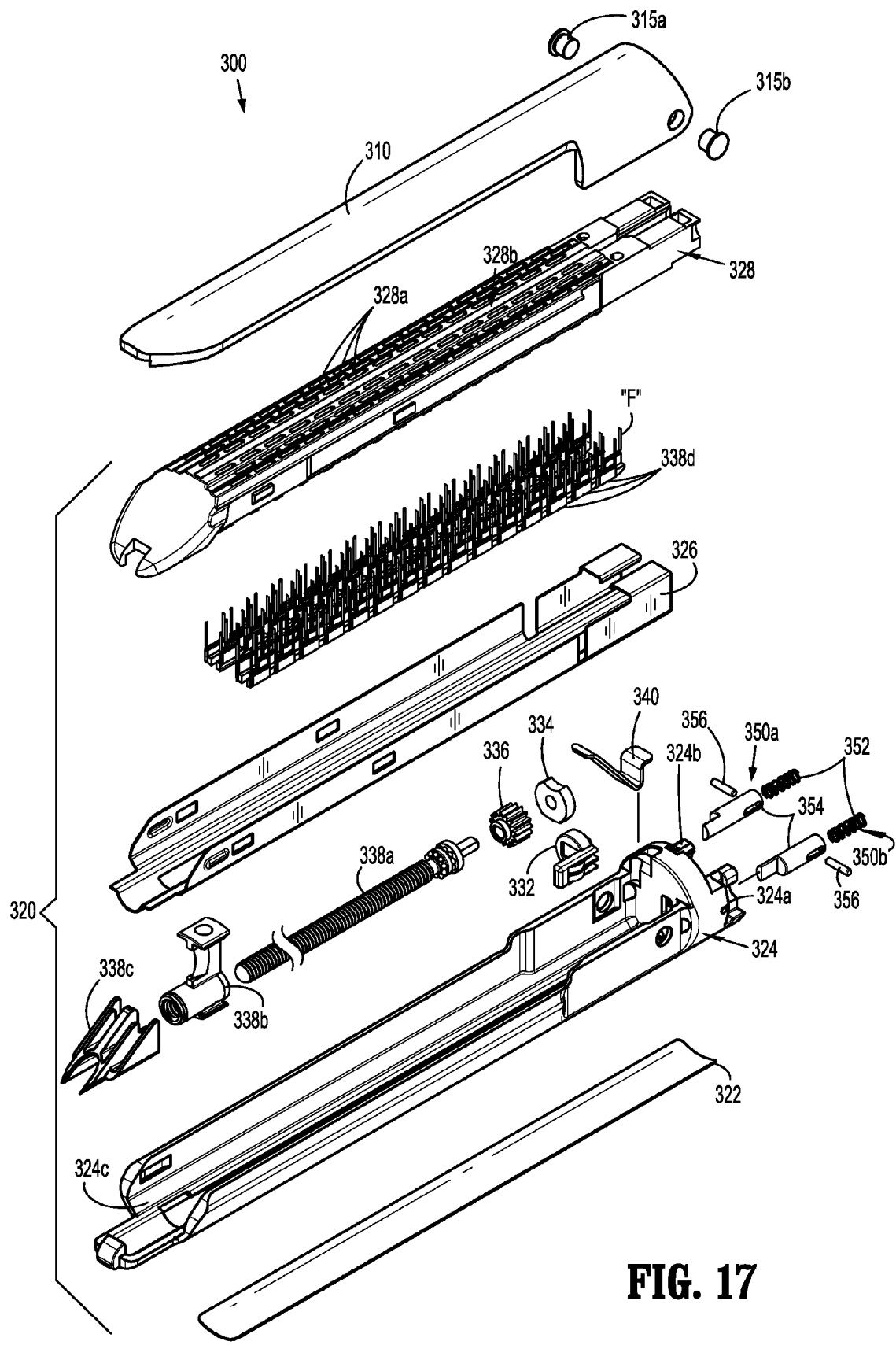
FIG. 17 is an enlarged, perspective view, with parts separated, of a surgical loading unit of the electromechanical surgical system of FIG. 1A.

Turning now to FIG. 17, loading unit 300 includes anvil 310 and cartridge assembly 320 that are pinned together by a pair of pins 315a, 315b and movable between open and closed conditions. Anvil 310 and cartridge assembly 320 cooperate to apply a plurality of linear rows of fasteners "F" (e.g., staples). In certain embodiments, the fasteners are of various sizes, and, in certain embodiments, the fasteners have various lengths or rows, e.g., about 30, 45 and 60 mm in length.

Cartridge assembly 320 includes a base 322 secured to a mounting portion 324, a frame portion 326, and a cartridge portion 328 defining a plurality of fastener retaining slots 328a and a knife slot 328b in a tissue engaging surface thereof. Mounting portion 324 has mating surfaces 324a, 324b on a proximal end thereof and defines a receiving channel 324c therein that supports frame portion 326, cartridge portion 328, and a fastener firing assembly 330 therein. Cartridge assembly 320 supports a biasing member 340 that engages anvil 310.

Fastener firing assembly 330 includes an electrical contact member 332 in electrical communication with circuit board of surgical device 100 (FIG. 1A), a bearing member 334, a gear member 336 that engages gear 2050 of distal end portion 2040 of outer tube 204, and a screw assembly 338. Screw assembly 338 includes a lead screw 338a, a drive beam 338b, and an actuation sled 338c that is engagable with a plurality of pusher members 338d.

Cartridge assembly 320 also supports a pair of plunger assemblies 350a, 350b. Each of the pair of plunger assemblies 350a, 350b includes a spring 352, a plunger 354, and a pin 356 that secures each plunger assembly to mounting portion 324. Plunger assemblies 350a, 350b cooperate with the proximal end of cartridge portion 328 to facilitate securement of cartridge portion 328 within mounting portion 324.

Figure 18:
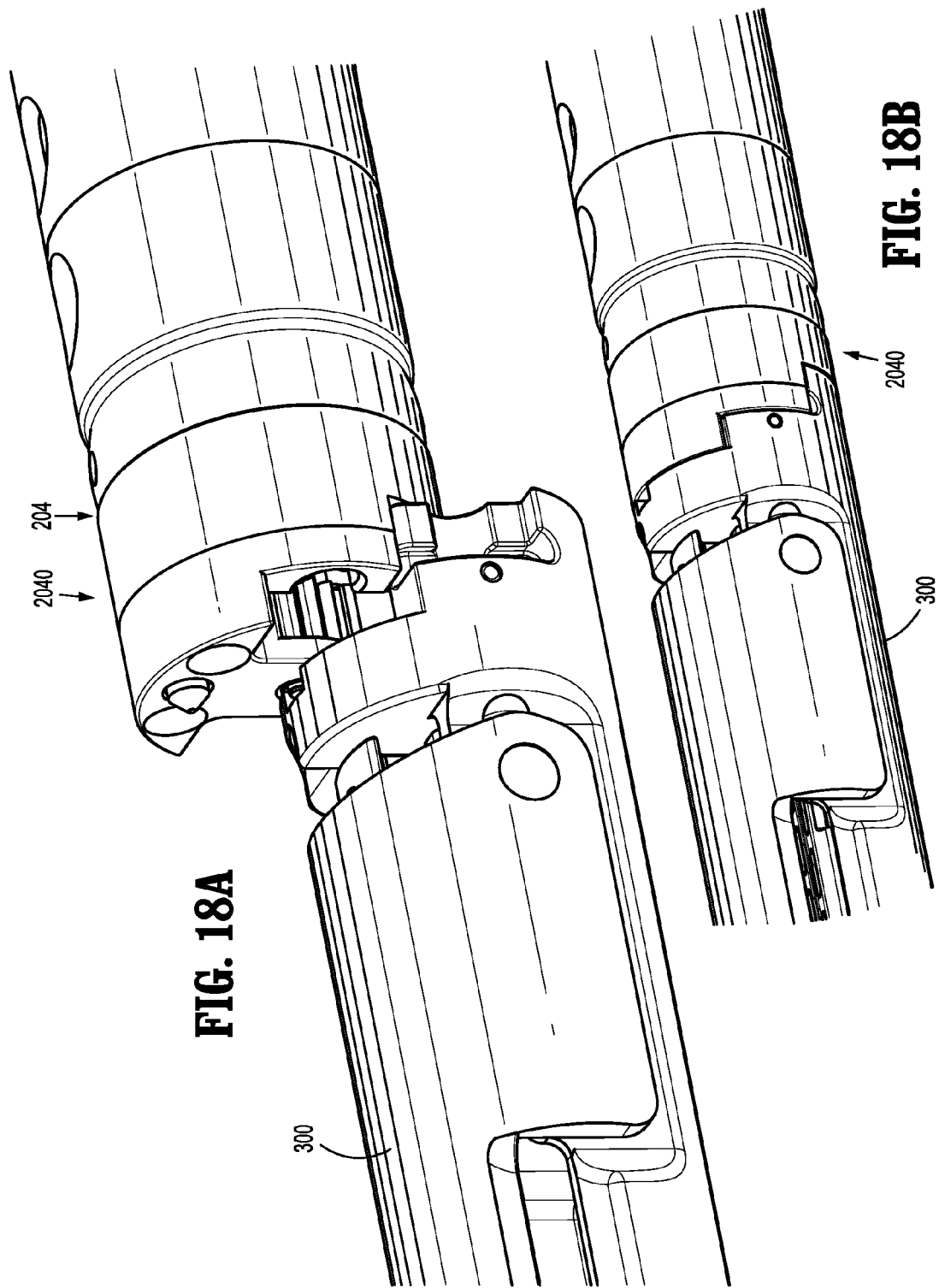
FIGS. 18A and 18B are progressive, side, perspective views illustrating a proximal portion of a surgical loading unit of the electromechanical surgical system of FIG. 1A being secured to the distal portion of the adapter assembly shown in FIG. 3.

In order to secure the proximal end of loading unit 300 to distal end portion 2040 of outer tube 204, the proximal end of loading unit 300 is aligned with distal end portion 2040 of outer tube 204 as seen in FIG. 18A so that the proximal end of loading unit 300 can be snapped together with distal end portion 2040 as seen in FIG. 18A. Referring also to FIGS. 10 and 17, mating surfaces 324a, 324b of loading unit 300 engage with mating surfaces 2048h of fourth segment 2048 so that the teeth of gear member 336 of loading unit 300 enmesh with the teeth of gear 2050.

Figure 19:
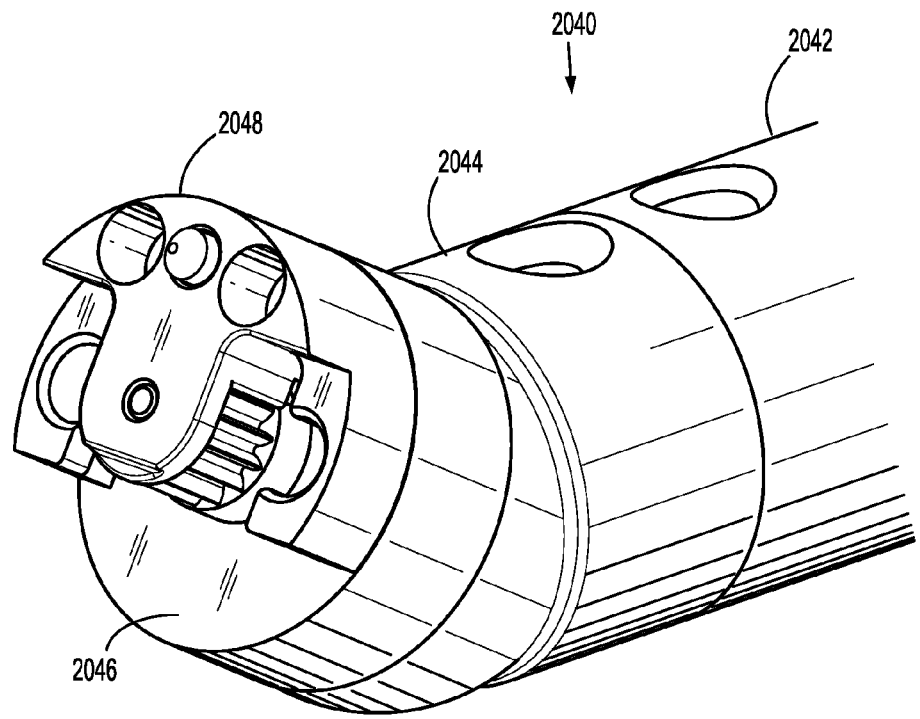
FIG. 19 is an enlarged, front, perspective view of the distal end portion of the adapter assembly of FIG. 3, the distal end portion of the adapter assembly being shown in an articulated condition.
Figure 20:
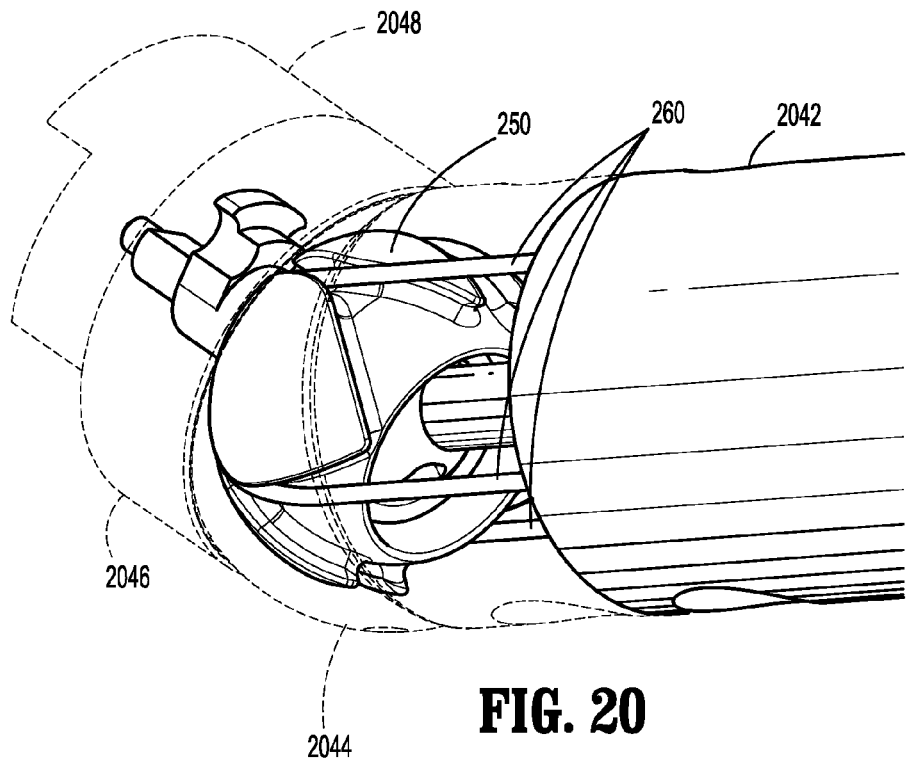
FIG. 20 is an enlarged, rear, perspective view of the distal end portion of the adapter assembly of FIG. 3 with portions thereof removed for clarity, the distal end portion of the adapter assembly being shown in the articulated condition.
Figure 21:
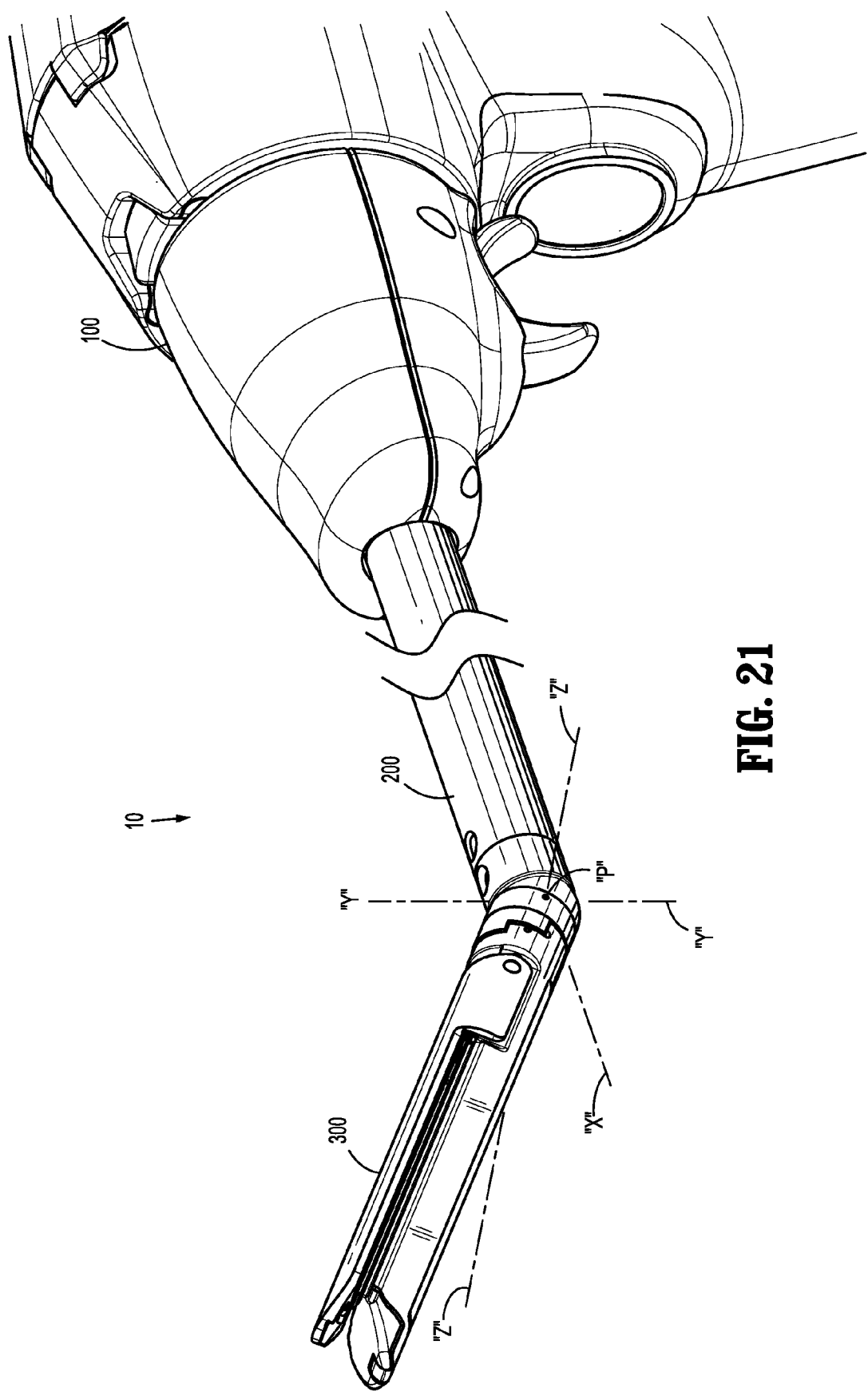
FIG. 21 is an enlarged, front, perspective view of a portion of the electromechanical surgical system of FIG. 1A, the surgical loading unit thereof being shown in the articulated condition.

In operation, depression of articulating pad 108 contacts one more of the plurality of sensors 108a to electrically communicate with the circuit board, activate one or both of rotatable drive shafts 106a, 106c (due to an actuation of a motor (not shown) within handle housing 102), and effectuate rotation of threaded screw assembly 244 of one or both of the pair of sleeve assemblies 240a, 240b. In particular, rotation of each threaded screw assembly 244 is effectuated by virtue of rotational engagement between input socket 244b of one of the pair of sleeve assemblies 240a, 240b and one of rotatable drive shafts 106a, 106c. Rotation of threaded screw 244a axially moves the pair of threaded sleeves 246, 248 along the respective support shaft between an approximated condition (see FIG. 9) and a separated condition (see FIG. 4), as illustrated by lines "C1," "C2," "C3," and "C4" shown in FIG. 7. Relative axial movement of the pair of threaded sleeves 246, 248 proximally draws/retracts/tightens one/a first cable of one of the opposite pairs of cables (e.g., first cable 260a and fourth cable 260d being a first opposite pair of cables, and second cable 260b and third cable 260c being a second opposite pair of cables) of the plurality of cables 260 and distally lets out/extends/releases another/a second cable of one of the opposite pairs of cables to rotate/pivot/articulate gimbal 250. As gimbal 250 rotates, distal portion 250b of gimbal 250 engages cylindrical body 2046a and/or U-shaped shoe 2046b of third segment 2046 to articulate distal end portion 2040 relative to outer tube 204 about longitudinal axis "X." Movement of distal end portion 2040 articulates loading unit 300 relative to outer tube 204 about longitudinal axis "X" in any direction (e.g., omni-directionally) as seen in FIGS. 19-21. More particularly, while longitudinally fixed to the distal end of outer tube 204 (and first and second segments 2042, 2044 of distal end portion 2040), loading unit 300 (and third and fourth segments 2046, 2048 of distal end portion 2040) can be articulated in any direction relative to "X," "Y," and/or "Z" axes that extend from a central point "P" defined in the distal end portion 2040 to position loading unit 300 at any desired orientation.

Tension/slack in one or more of the plurality of cables 260 may need to be adjusted, for example, before, during, and/or after one or more uses of system 10. To effectuate a tightening and/or loosening of slack/tension, one or both actuators 107a, 107b (see FIG. 1A), can be actuated to impart rotational movement to one or both of rotatable drive members 106d, 106e. With rotatable drive members 106d, 106e in engagement with proximal ends of screws 243, rotation of rotatable drive members 106d, 106e causes one or both of screws 243 to rotate. Rotation of one or both screws 243 adjusts tension in one or more of the plurality of cables 260 by moving one or both of the plurality of the pair of sleeve assemblies 240a, 240b as described above.

To fire the plurality of fasteners "F," firing trigger 205 of adapter assembly 200 is actuated so that trigger contact surface 205a contacts trigger contact surface 105 of handle housing 102 to rotate rotatable drive member 106b (due to an activation of a motor (not shown) within handle housing 102). Rotation of rotatable drive member 106b causes proximal firing shaft 274 to rotate with distal firing shaft 276 about longitudinal axis "X" such that gear 2050 rotates gear 336 of loading unit 300. Rotation of gear 336 rotates lead screw 338a and enables drive beam 338a to axially advance along lead screw 338a and through longitudinal knife slot 328b by virtue of the threaded engagement between lead screw 338a and drive beam 338a. Drive beam 338a engages anvil 310 to maintain anvil and cartridge assembly 310, 320 in approximation. Distal advancement of drive beam 338b advances actuation sled 338c into engagement with the plurality of pusher members 328 and fires the plurality of fasteners "F" from the plurality of fastener retention slots 328a for forming against corresponding fastener forming pockets defined within anvil 310. Loading unit 300 can be reset and fastener cartridge 328 can be replaced so that loading unit 300 can then be re-fired as desired.

Figure 22:
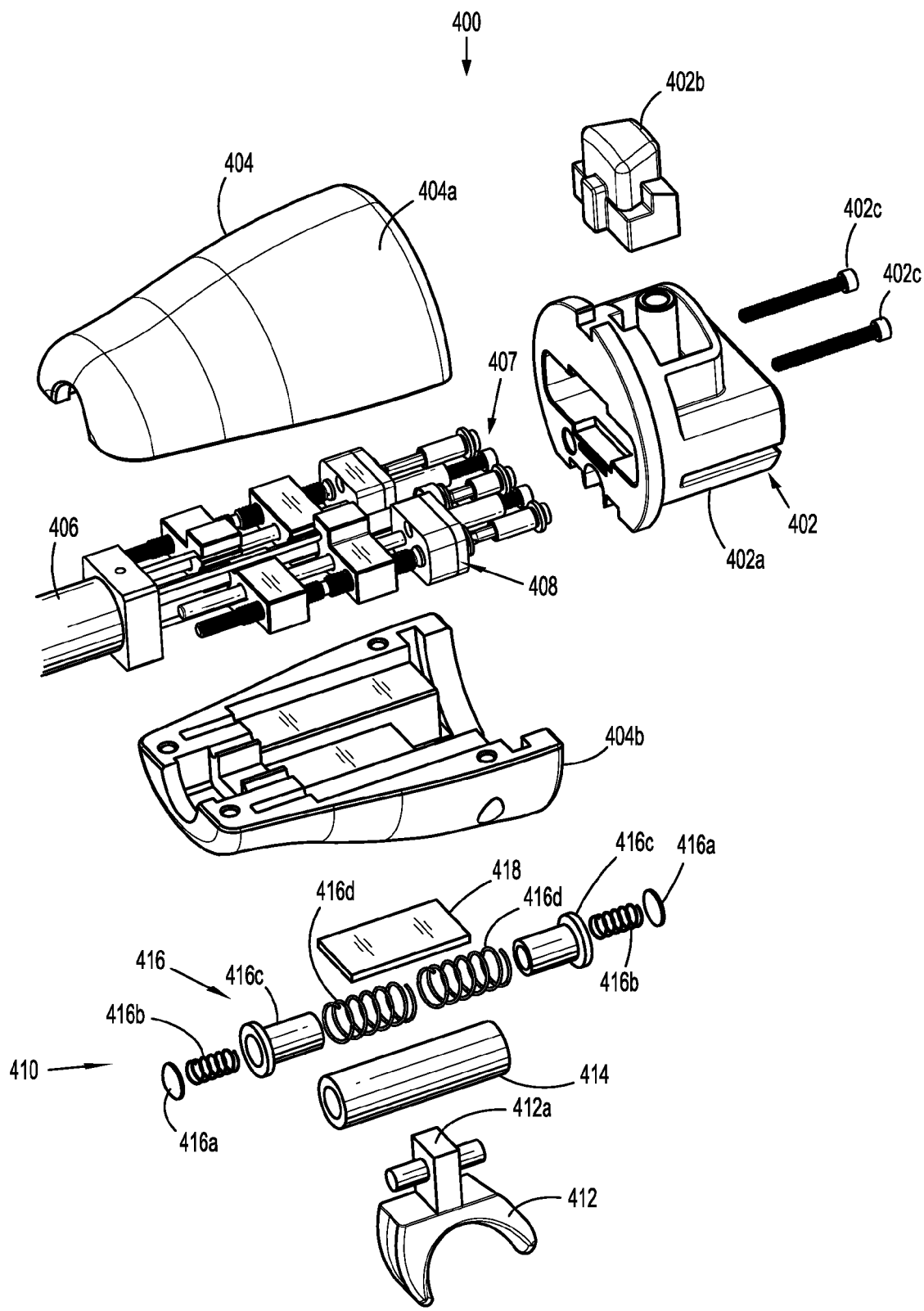
FIG. 22 is a side, perspective view, with parts separated, of a proximal portion of another embodiment adapter assembly in accordance with the present disclosure.

Turning now to FIG. 22, a proximal portion of another embodiment of an adapter assembly is provided and generally referred to as 400. Adapter assembly 400 is substantially similar to adapter assembly 200 and is only described herein to the extent necessary to describe the differences in construction and operation thereof. Adapter assembly 400 includes a proximal housing assembly 402, a distal housing assembly 404, an outer tube 406, a firing shaft assembly 407, an articulation assembly 408, and a trigger assembly 410. Proximal housing assembly 402 includes a proximal housing 402a, a release button 402b, and a pair of screws 402c that couple to the articulation assembly 400. Distal housing assembly 404 includes a first-half section 404a and a second-half section 404b that couple to proximal housing assembly 402 and support a proximal portion of articulation assembly 408.

Figure 23:
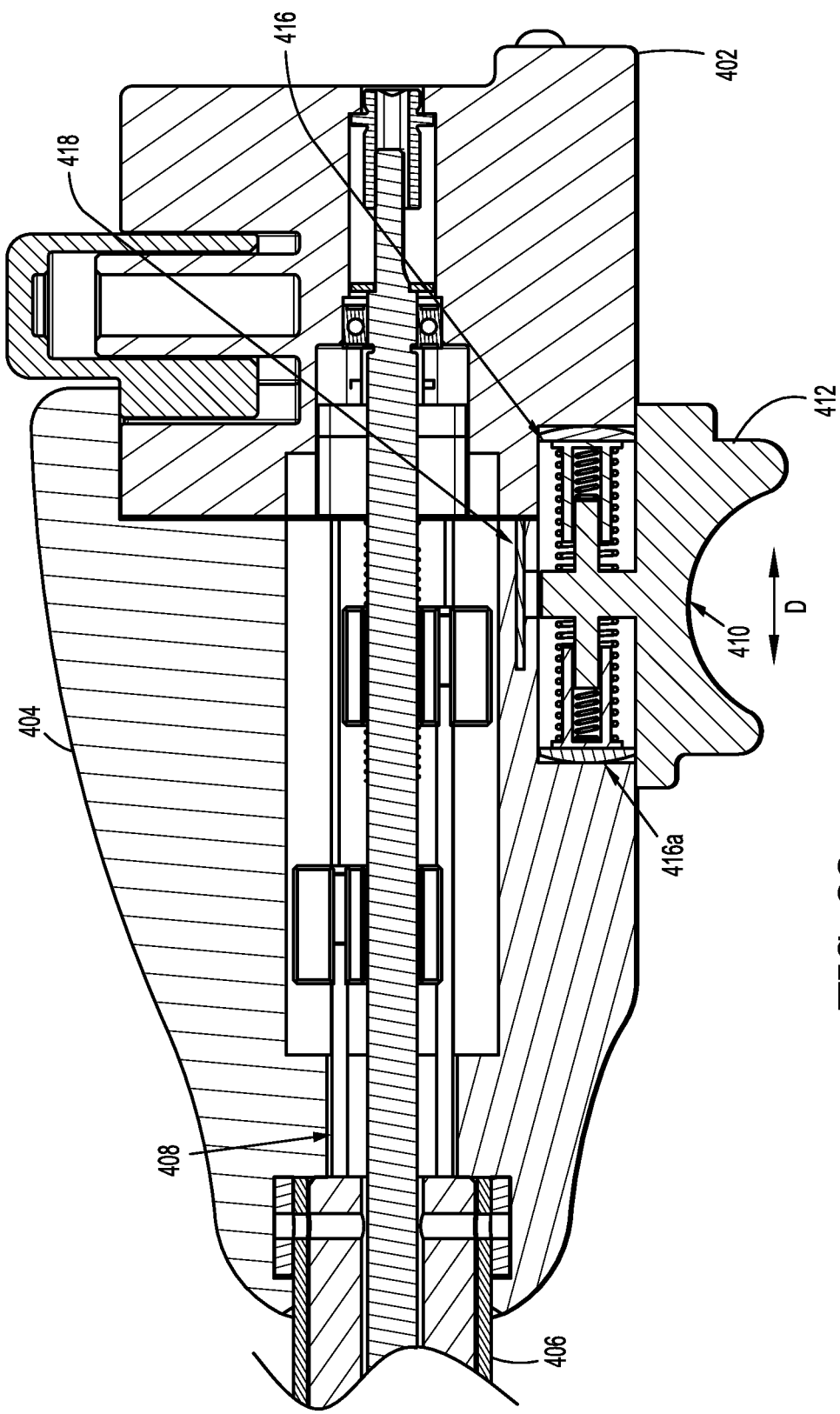
FIG. 23 is a side, cross-sectional view of the proximal portion of the adapter assembly of FIG. 22.

Trigger assembly 410 includes a trigger 412 with a magnetic area 412a, support tube 414, a switch assembly 416, and a hall effect switch (PCB) 418. Switch assembly 416 includes a pair of tactile domes 416a, a pair of inner springs 416b, a pair of plungers 416c, and a pair of outer springs 416d. The pairs of inner and outer springs 416b, 416d cooperate with the pair of plungers 416c to bias trigger 410 to a centered position (see FIG. 23). As illustrated by line "D," trigger 412 is axially movably supported within distal and proximal housings 402, 404 and actuatable to move magnetic area 412a of trigger 412. The pair of tactile domes 416a is configured to provide an audible click as the pair of plungers 416c contact the pair of tactile domes 416a to indicate an end of trigger travel.

In operation, movement of magnetic area 412a of trigger 412 relative to Hall Effect switch 418 creates a magnetic field and generates an electrical signal that communicates with the circuit board of surgical instrument 100 to activate rotatable drive member 106b of surgical instrument 100. Rotation of rotatable drive member 106b rotates firing shaft assembly 407 to fire loading unit 300 as describe above.

Any of the components described herein may be fabricated from either metals, plastics, resins, composites or the like taking into consideration strength, durability, wearability, weight, resistance to corrosion, ease of manufacturing, cost of manufacturing, and the like.

In embodiments, any of the components described herein, such as the end effector and/or adapter, can include one or more microchips, such as, for example a one-wire microchip (e.g., microchip model nos. DS2465, DS28E15, and/or DS2432, available from MAXIM INTEGRATED™, San Jose, Calif.) that electrically couple to the circuit board/controller of surgical device 100. Exemplary one-wire microchips are shown and described in U.S. Pat. No. 6,239,732, the entire content of which is incorporated herein by reference. Any of these chips can include encrypted authentication (e.g., SULU ID) and/or may be one wire compatible.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An adapter assembly for selectively interconnecting a surgical loading unit that is configured to perform a function and a surgical device that is configured to actuate the surgical loading unit, the surgical loading unit including an axially translatable drive member, and the surgical device including a plurality of rotatable drive shafts, the adapter assembly comprising:
  a housing configured and adapted for connection with the surgical device and to be in operative communication with each rotatable drive shaft of the plurality of rotatable drive shafts of the surgical device;

an outer tube having a proximal end supported by the housing and a distal end configured and adapted for connection with the surgical loading unit, wherein the distal end of the outer tube is in operative communication with the axially translatable drive member of the surgical loading unit, the outer tube defining a longitudinal axis; and an articulation assembly including a gimbal supported in the outer tube and a plurality of threaded sleeves supported in the housing, the plurality of threaded sleeves coupled to the gimbal by at least one cable, wherein rotation of at least one of the plurality of rotatable drive shafts of the surgical device translates at least two of the plurality of threaded sleeves to omni-directionally articulate the gimbal relative to the longitudinal axis of the outer tube with the at least one cable, and wherein articulation of the gimbal articulates the surgical loading unit about the distal end of the outer tube.

2. The adapter assembly of claim 1, further including a firing shaft having a proximal end configured and adapted to couple to at least one of the plurality of rotatable drive shafts of the surgical device and a distal end configured and adapted to couple to the axially translatable drive member of the surgical loading unit to enable firing of the surgical loading unit.

3. The adapter assembly of claim 2, wherein the firing shaft is configured and adapted to transmit a rotational force through the gimbal to effectuate axially translation of the axially translatable drive member and fire the surgical loading unit.

4. The adapter assembly of claim 3, wherein the firing shaft includes a proximal firing shaft and a distal firing shaft, the proximal and distal firing shafts coupled together within the gimbal such that the distal firing shaft is movable relative to the proximal firing shaft.

5. The adapter assembly of claim 4, wherein the proximal firing shaft includes a ball member on a distal end thereof and the distal firing shaft includes a socket on a proximal end thereof, the socket defining a socket bore, the ball member of the proximal firing shaft being mounted within the socket bore.

6. The adapter assembly of claim 5, wherein the gimbal defines a gimbal bore therethrough configured and adapted to receive the distal firing shaft such that the gimbal and the distal firing shaft are movable about an outer surface of the ball member.

7. The adapter assembly of claim 1, wherein the gimbal defines at least one slot in an outer surface thereof, the at least one cable being secured within the at least one slot.

8. The adapter assembly of claim 1, wherein the outer tube includes a distal housing assembly configured and adapted to engage a proximal end of the surgical loading unit, and the gimbal includes a distal flange configured and adapted to engage the distal housing assembly to enable the surgical loading unit to articulate in response to movement of the gimbal.

9. The adapter assembly of claim 1, wherein the plurality of threaded sleeves is supported on at least one threaded screw.

10. The adapter assembly of claim 9, wherein the at least one threaded screw includes a first set of threads and a second set of threads, the first and second set of threads being threaded in opposite directions, wherein a first one of the plurality of threaded sleeves is threadably engaged with the first set of threads and a second one of the plurality of threaded sleeves is threadably engaged with the second set of threads, wherein rotation of the at least one threaded screw in a first rotational direction approximates the first one and the second one of the plurality of threaded sleeves, and wherein rotation of the at least one threaded screw in a second rotational direction separates the first one and the second one of the plurality of threaded sleeves.

11. The adapter assembly of claim 1, further including a firing trigger secured to the housing.

12. An electromechanical surgical system, comprising:
a surgical loading unit including at least one axially translatable drive member;
a handle-held electromechanical surgical device including:
a housing; and
at least one rotatable drive shaft supported in the housing; and
an adapter assembly selectively connectable between the housing of the surgical device and the surgical loading unit, the adapter assembly including:
an articulation assembly including a gimbal and a plurality of threaded sleeves, the plurality of threaded sleeves coupled to the gimbal by at least one cable, the plurality of threaded sleeves being movable to articulate the gimbal with the at least one cable, wherein articulation of the gimbal articulates the surgical loading unit; and
a firing shaft connectable between the at least one rotatable drive shaft of the surgical device and the at least one axially translatable drive member, the firing shaft being movable with the gimbal to omni-directionally articulate the surgical loading unit and rotatable to translate the at least one axially translatable drive member through the surgical loading unit.

13. The electromechanical surgical system of claim 12, wherein the firing shaft includes a proximal firing shaft and a distal firing shaft, the proximal and distal firing shafts coupled together within the gimbal such that the distal firing shaft is movable relative to the proximal firing shaft.

14. The electromechanical surgical system of claim 13, wherein the proximal firing shaft includes a ball member on a distal end thereof and the distal firing shaft includes a socket on a proximal end thereof, the socket defining a socket bore, the ball member of the proximal firing shaft being mounted within the socket bore.

15. The electromechanical surgical system of claim 14, wherein the gimbal defines a gimbal bore therethrough configured and adapted to receive the distal firing shaft such that the gimbal and the distal firing shaft are movable about an outer surface of the ball member.

16. The electromechanical surgical system of claim 12, wherein the gimbal defines at least one slot in an outer surface thereof, the at least one cable being secured within the at least one slot.

17. The electromechanical surgical system of claim 12, wherein the gimbal includes a distal flange configured and adapted to enable the surgical loading unit to articulate in response to movement of the gimbal.

18. The adapter assembly of claim 12, wherein the plurality of threaded sleeves is supported on at least one threaded screw.

19. The adapter assembly of claim 18, wherein the at least one threaded screw includes a first set of threads and a second set of threads, the first and second set of threads being threaded in opposite directions, wherein a first one of the plurality of threaded sleeves is threadably engaged with the first set of threads and a second one of the plurality of threaded sleeves is threadably engaged with the second set of threads, wherein rotation of the at least one threaded screw in a first rotational direction approximates the first one and the second one of the plurality of threaded sleeves, and wherein rotation of the at least one threaded screw in a second rotational direction separates the first one and the second one of the plurality of threaded sleeves.

20. The adapter assembly of claim 12, wherein a firing trigger is secured to the adapter assembly.

* * * * *